United States Patent
Ezra et al.

(10) Patent No.: US 12,098,362 B2
(45) Date of Patent: *Sep. 24, 2024

(54) **USES OF *DALDINIA* SP. OR VOLATILE ORGANIC COMPOUNDS DERIVED THEREFROM**

(71) Applicant: THE STATE OF ISRAEL, MINISTRY OF AGRICULTURE & RURAL DEVELOPMENT, AGRICULTURE RESEARCH ORGANIZATION (ARO) (VOLCANI CENTER), Beit Dagan (IL)

(72) Inventors: David Ezra, Ein-Vered (IL); Orna Liarzi, Rehovot (IL)

(73) Assignee: THE STATE OF ISRAEL, MINISTRY OF AGRICULTURE & RURAL DEVELOPMENT, AGRICULTURAL RESEARCH ORGANIZATION (ARO) (VOLCANI CENTER), Beit Dagan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/547,853

(22) PCT Filed: Feb. 2, 2016

(86) PCT No.: PCT/IL2016/050116
§ 371 (c)(1),
(2) Date: Aug. 1, 2017

(87) PCT Pub. No.: WO2016/125153
PCT Pub. Date: Aug. 11, 2016

(65) Prior Publication Data
US 2018/0014547 A1 Jan. 18, 2018

Related U.S. Application Data

(60) Provisional application No. 62/110,665, filed on Feb. 2, 2015.

(51) Int. Cl.
*C12N 1/14* (2006.01)
*A01N 63/30* (2020.01)
*A61K 36/062* (2006.01)
*C12P 1/02* (2006.01)

(52) U.S. Cl.
CPC ............... *C12N 1/14* (2013.01); *A01N 63/30* (2020.01); *A61K 36/062* (2013.01); *C12P 1/02* (2013.01)

(58) Field of Classification Search
CPC .................................................... A01N 63/04
See application file for complete search history.

(56) References Cited

U.S. PATENT DOCUMENTS

| | | | |
|---|---|---|---|
| 4,275,234 A | 6/1981 | Baniel et al. | |
| 5,476,832 A | 12/1995 | Miller et al. | |
| 5,510,526 A | 4/1996 | Baniel et al. | |
| 5,641,406 A | 6/1997 | Sarhaddar et al. | |
| 5,831,122 A | 11/1998 | Eyal | |
| 6,855,669 B2 | 2/2005 | Knowles et al. | |
| 7,135,449 B2 | 11/2006 | Li et al. | |
| 7,267,975 B2 | 9/2007 | Strobel et al. | |
| 7,341,862 B2 | 3/2008 | Strobel et al. | |
| 7,754,203 B2 | 7/2010 | Strobel et al. | |
| 8,728,462 B2 | 5/2014 | Gandhi et al. | |
| 2004/0053787 A1* | 3/2004 | Knowles ................ A01N 35/02 504/348 |
| 2004/0141955 A1 | 7/2004 | Strobel et al. | |
| 2004/0185031 A1 | 9/2004 | Strobel et al. | |
| 2006/0089263 A1 | 4/2006 | Rodriguez-Kabana et al. | |
| 2007/0072945 A1 | 3/2007 | Kumar et al. | |
| 2007/0155830 A1 | 7/2007 | Liu et al. | |
| 2007/0202141 A1 | 8/2007 | Jumean et al. | |
| 2009/0142816 A1 | 6/2009 | Strobel | |
| 2009/0246293 A1 | 10/2009 | Ehr et al. | |
| 2011/0287471 A1 | 11/2011 | Strobel et al. | |
| 2011/0302823 A1 | 12/2011 | Bruck et al. | |
| 2012/0252893 A1 | 10/2012 | Pimentel | |
| 2013/0005807 A1 | 1/2013 | Ishida et al. | |
| 2013/0028844 A1 | 1/2013 | Bilgic | |
| 2013/0137131 A1 | 5/2013 | Strobel et al. | |

(Continued)

FOREIGN PATENT DOCUMENTS

| CN | 102885078 A | 1/2013 |
|---|---|---|
| CN | 103025157 A | 4/2013 |

(Continued)

OTHER PUBLICATIONS

Anke, H., Secondary metabolites with nematicidal and antimicrobial activity from nematophagous fungi and Ascomycetes, 1995, Canadian Journal of Biology, vol. 73, vol. 1, S932-S939 (Year: 1995).*

(Continued)

*Primary Examiner* — Abigail Vanhorn
*Assistant Examiner* — Ali S Saeed
(74) *Attorney, Agent, or Firm* — BROWDY AND NEIMARK, PLLC

(57) ABSTRACT

A method of killing a phytopathogen or reducing growth thereof is provided. The method comprising exposing the phytopathogen to an effective amount of a composition comprising a biologically pure culture of *Daldinia* sp. or at least one volatile organic compound (VOC) being produced by the biologically pure culture and capable of killing the phytopathogen or reducing growth thereof.

13 Claims, 16 Drawing Sheets

Specification includes a Sequence Listing.

(56) References Cited

U.S. PATENT DOCUMENTS

| | | |
|---|---|---|
| 2013/0224315 A1 | 8/2013 | Green et al. |
| 2013/0252289 A1 | 9/2013 | Strobel et al. |
| 2013/0252313 A1 | 9/2013 | Strobel et al. |
| 2013/0323781 A1 | 12/2013 | Moularat et al. |
| 2013/0345053 A1 | 12/2013 | Schreuder |
| 2014/0086879 A1 | 3/2014 | Strobel et al. |
| 2014/0107219 A1 | 4/2014 | Watkins et al. |
| 2014/0271534 A1 | 9/2014 | Wu et al. |
| 2014/0274683 A1 | 9/2014 | Wu et al. |
| 2014/0323572 A1 | 10/2014 | Pimentel et al. |
| 2015/0031762 A1 | 1/2015 | Pimentel et al. |
| 2015/0128864 A1 | 5/2015 | Bolckmans et al. |
| 2016/0100597 A1 | 4/2016 | Immaraju et al. |

FOREIGN PATENT DOCUMENTS

| | | | |
|---|---|---|---|
| CN | 103328639 A | 9/2013 | |
| CN | 104823973 A | 8/2015 | |
| CN | 104823989 A | 8/2015 | |
| EP | 388122 A1 | 9/1990 | |
| FR | 2437836 A1 * | 4/1980 | ........... A61K 36/062 |
| GB | 998360 A | 7/1965 | |
| GB | 1026361 A | 4/1966 | |
| GB | 1529279 A | 10/1978 | |
| KR | 20040010986 A * | 2/2004 | |
| WO | 9300440 A1 | 1/1993 | |
| WO | 0062792 A2 | 10/2000 | |
| WO | 2005009360 A2 | 2/2005 | |
| WO | 2006094371 A2 | 9/2006 | |
| WO | 2009146079 A2 | 12/2009 | |
| WO | 2012031174 A2 | 3/2012 | |
| WO | 2013081777 A1 | 6/2013 | |
| WO | 2013156492 A2 | 10/2013 | |
| WO | 2014190108 A1 | 11/2014 | |
| WO | 2015089661 A1 | 6/2015 | |
| WO | 2016042389 A1 | 2/2016 | |
| WO | 2016125153 A1 | 8/2016 | |
| WO | 2017027836 A1 | 2/2017 | |

OTHER PUBLICATIONS

Chitwood, D., Phytochemical Based Strategies for Nematode Control, 2002, Annual. Review of Phytopathology, vol. 40, pp. 221-229. (Year: 2002).*

Pike, T.J., Interactions Between the Invasive Brown Marmorated Stink Bug, *Halyomorpha halys* (Hemiptera: Pentatomidae), and Entomopathogenic Fungi, 2014, Master Thesis, 58 pages. (Year: 2014).*

Benoit, Joshua, Addition of Alarm Pheromone Components Improcves the Effectiveness of Desiccant Dusts Against Cimex lectularius, Jun. 2009, Journal of Medical Entomology, vol. 46, Issue 3, pp. 572-579. (Year: 2009).*

2-Octenal, Compound Summary,[online]. PubChem, 2019 [retrieved Dec. 23, 2019]. Retrieved from the Internet:<https://pubchem.ncbi.nlm.nih.gov/compound/5283324#section=InChl-Key>, 2 pages. (Year: 2019).*

Emulsifier (nonionic), Industrial and Consumer Specialties Crop Protection Brochure, 2012, Clariant, 14 pages. (Year: 2012).*

Alkyl Radical, Definition [online]. The Free Dictionary by Farlex, 2020 [retrieved on Sep. 9, 2020]. Retrieved from the Internet:<URL: https://www.thefreedictionary.com/alkyl+radical>, 2 pages (Year: 2020).*

Alkyl Group, Definition [online]. The Free Dictionary by Farlex, 2020 [retrieved on Sep. 9, 2020]. Retrieved from the Internet:<URL: https://www.thefreedictionary.com/alkyl+group (Year: 2020).*

Castillo et al. Antifungal properties of bioactive compounds from plants, Jan. 2012, Fungicides for plant and animal diseases (Year: 2012).*

Megan Kennelly, Tomato leaf and fruit diseases and disorders, May 2009, Kansas State University (Year: 2009).*

Shannon U. Morath "Fungal volatile organic compounds: A review with emphasis on their biotechnological potential", Fungal Biology Reviews, 2012, vol. 26, p. 73-83.

International Search Report of PCT/IL2016/050116 Completed May 16, 2016; Mailed Jun. 10, 2016 4 pages.

Written Opinion of ISR of PCT/IL2016/050116 Completed May 16, 2016; Mailed Jun. 10, 2016 9 pages.

Riyaz-Ul-Hassan et al., "An *Endophytic nodulisporium* sp. from Central America Producing Volatile Organic Compounds with Both Biological and Fuel Potential", J. Microbiol. Biotechnol. (2013), 23(1), 29-35.

Rahman et al., "In vitro antibacterial properties of essential oil and organic extracts of Premna integrifolia Linn" Arabian Journal of Chemistry, 1878-5352, 2011.

Kubo et al., "Antimicrobial Activity of the Olive Oil Flavor Compounds", J. Agric. Food Chem. 1995, 43, 1629-1633.

Costa et al., "Study on the chemical composition variability of some processed bergamot (*Citrus bergamia*) essential oils", Flavour and Fragrance Journal, 2010, 25, 4-12.

Battinelli et al., In vitro antifungal and anti-elastase activity of some aliphatic aldehydes from *Olea europaea* L. fruit, Phytomedicine, 13:558-563 (2006).

Kubo et al., Antimicrobial Activity of the Olive Oil Flavor Compounds, J. Agric. Food Chem., 43:1629-1633 (1995).

Hainer, Dermatophyte Infections, Am Fam Physician, 67(1):101-109 (2003).

Caboni, P., Ntalli, N. G., Aissani, N., Cavoski, I., & Angioni, A. (2012). Nematicidal Activity of (E,E)-2,4-Decadienal and (E)-2-Decenal from Ailanthus altissima against Meloidogyne javanica. Journal of Agricultural and Food Chemistry, 60 (4), 1146-1151. doi:10.1021/jf2044586.

Kim, J., Seo, S.- M., Lee, S.- G., Shin, S.- C., & Park, I.- K. (2008). Nematicidal Activity of Plant Essential Oils and Components from Coriander (*Coriandrum sativum*), Oriental Sweetgum (*Liquidambar orientalis*), and Valerian (*Valeriana wallichii*) Essential Oils against Pine Wood Nematode (*Bursaphelenchus xylophilus*). Journal of Agricultural and Food Chemistry, 56(16), 7316-7320. doi: 10.1021/jf800780f.

Liarzi, O., Bar, E., Lewinsohn, E., & Ezra, D. (2016). Use of the Endophytic Fungus Daldinia cf. concentrica and Its Volatiles as Bio-Control Agents. PLOS One, 11(12), e0168242. doi:10.1371/journal.pone.0168242.

Lu, H., Xu, S., Zhang, W., Xu, C., Li, B., Zhang, D., . . . Liu, F. (2017). Nematicidal Activity of trans-2-Hexenal against Southern Root-Knot Nematode (*Meloidogyne incognita*) on Tomato Plants. Journal of Agricultural and Food Chemistry, 65(3), 544-550. doi:10.1021/acs.jafc.6b04091.

* cited by examiner

Upper panel – the "Sandwich Method" in the presence of *D. concentrica*. The growth of *D. concentrica* can be seen under the *Aspergillus niger* plug. Lower panel – the growth of *A. niger* in control PDA plates in the absence of *D. concentrica*.

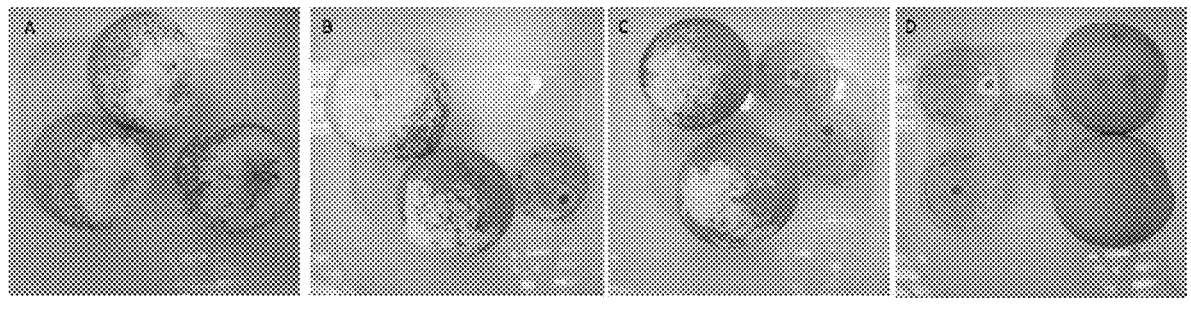
FIG. 8A     FIG. 8B     FIG. 8C     FIG. 8D
FIG. 9
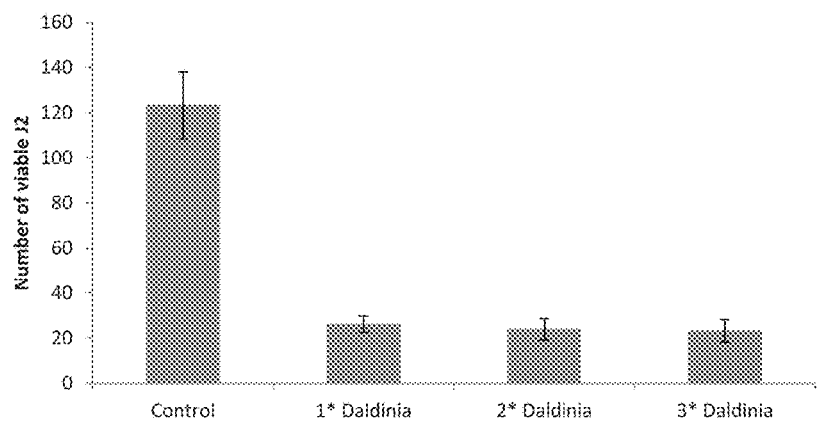
The numbers indicate the amount of 50 mm Petri plate containing 5 mL PDB and plug of *D. concentrica* used in the experiment.

FIG. 10

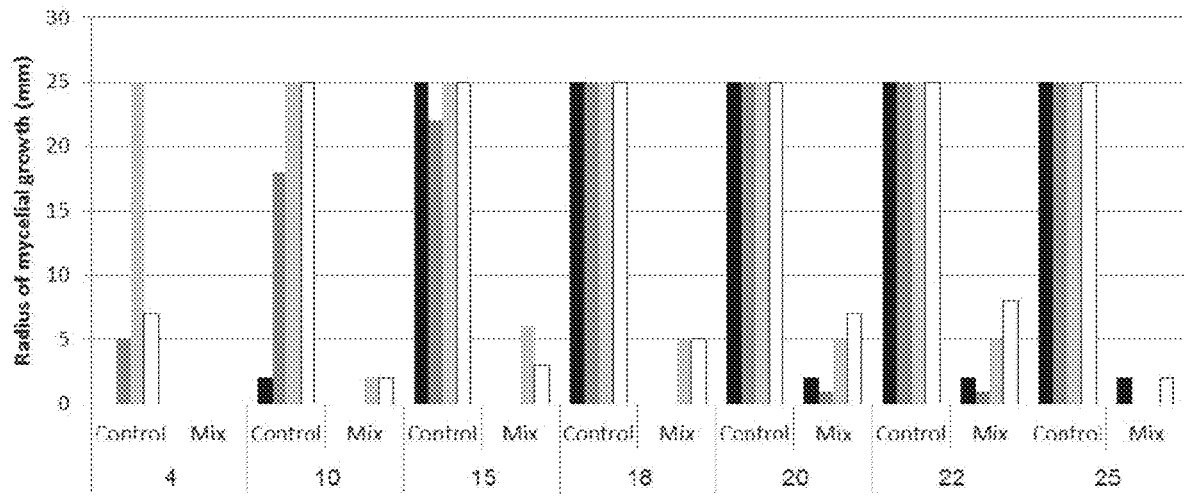

The numbers on the X axis indicate the temperature (°C). Black, dark gray, light gray and white columns represent mycelial growth after 14 days of *Aspergillus niger*, *Botrytis cinerea*, *Alternaria alternata* and *Penicillium digitatum*, respectively.

FIG. 11

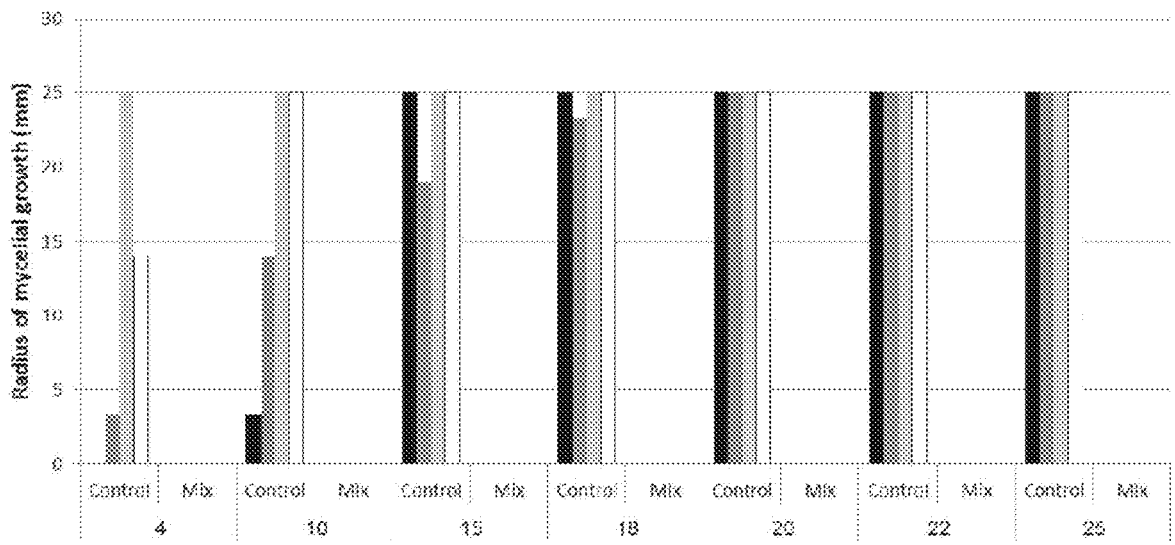

The numbers on the X axis indicate the temperature (°C). Black, dark gray, light gray and white columns represent mycelial growth after 14 days of *Aspergillus niger*, *Botrytis cinerea*, *Alternaria alternata* and *Penicillium digitatum*, respectively.

FIG. 13A 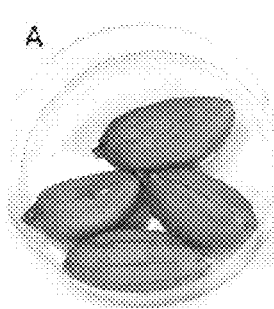 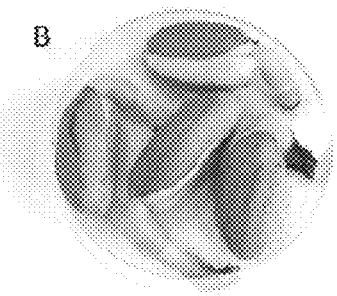 FIG. 13B
FIG. 13C 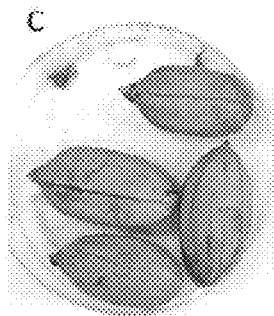 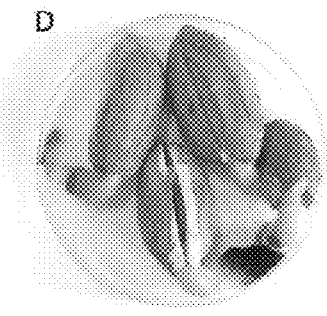 FIG. 13D
FIG. 13E 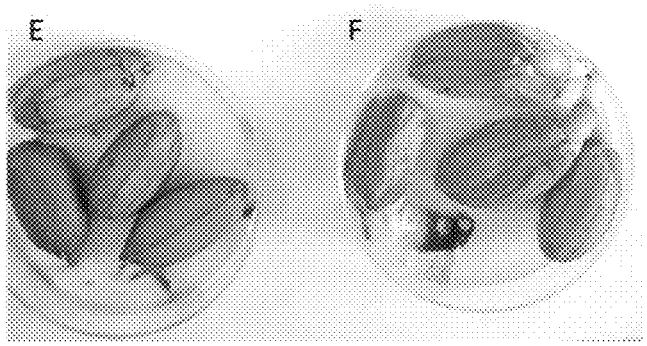 FIG. 13F FIG. 16A
FIG. 16B
FIG. 16C
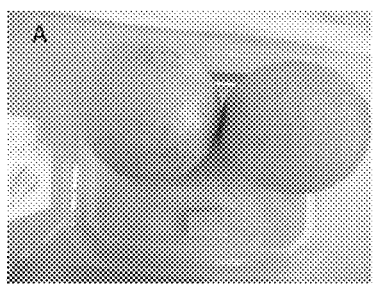
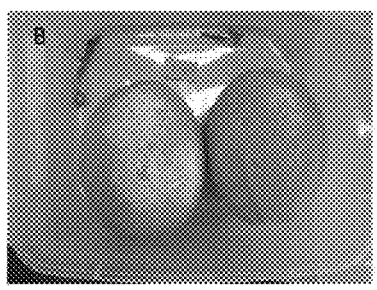
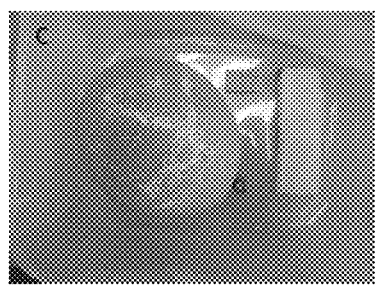
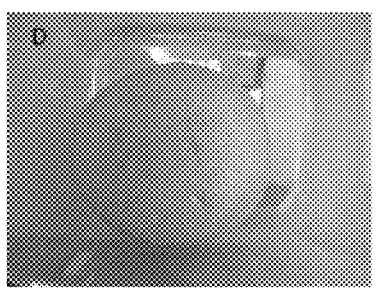
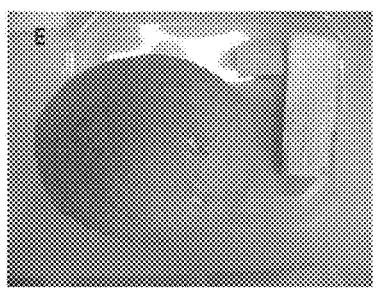
FIG. 16D
FIG. 16E
FIG. 17
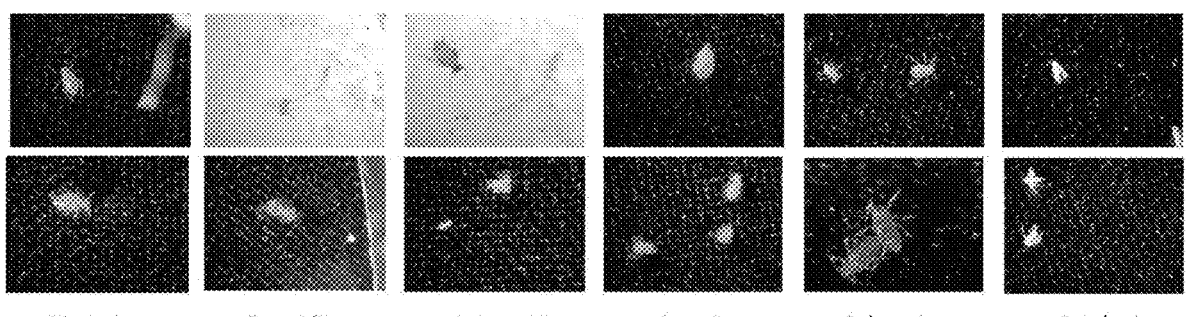
Upper panel – control; Lower panel – aphids after 15 minutes exposure to 0.125 µL/mL of "Mixture 21".

FIG. 18
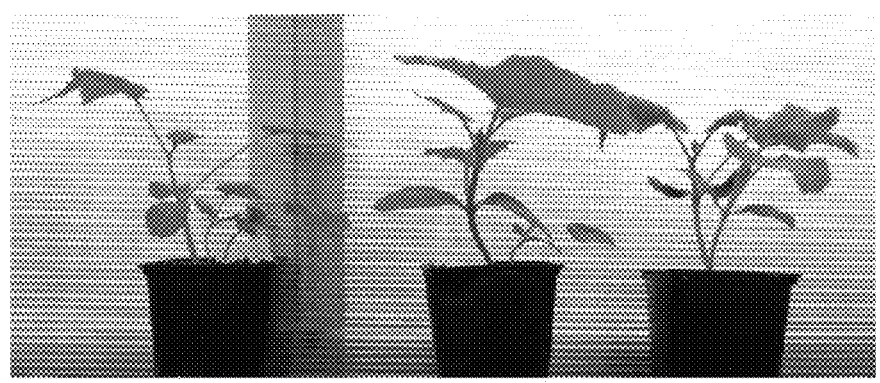
Control      0.083 µL/mL Mixture 21
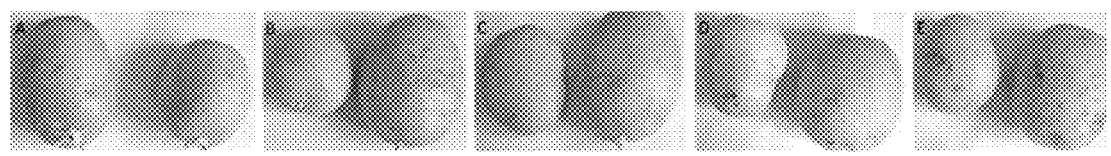
FIG. 19A    FIG. 19B    FIG. 19C    FIG. 19D    FIG. 19E FIG. 20A
FIG. 20B
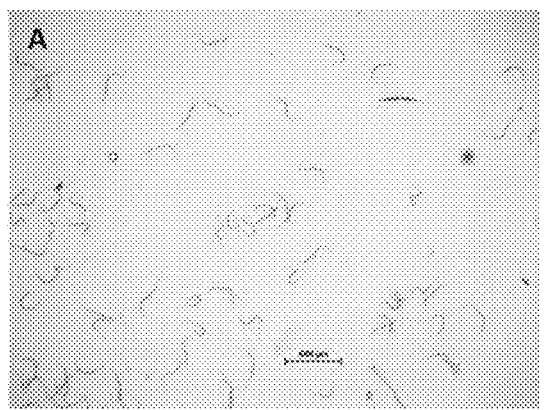
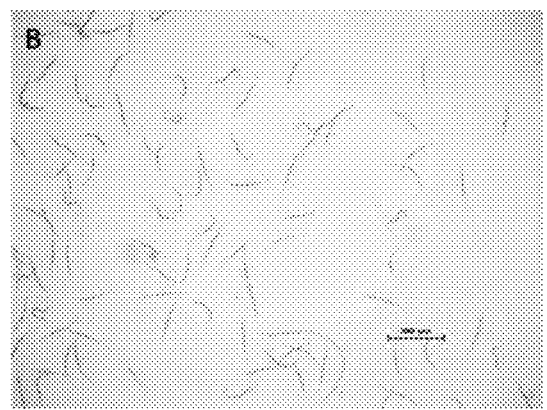
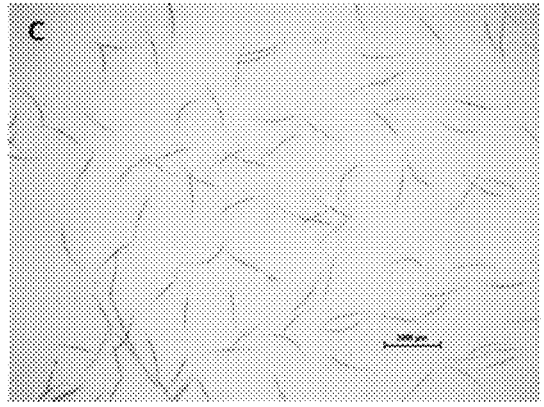
FIG. 20C
FIG. 20D

USES OF *DALDINIA* SP. OR VOLATILE ORGANIC COMPOUNDS DERIVED THEREFROM

RELATED APPLICATIONS

This application is a National Phase of PCT Patent Application No. PCT/IL2016/050116 having International filing date of Feb. 2, 2016, which claims the benefit of priority of U.S. Patent Application No. 62/110,665 filed on Feb. 2, 2015. The contents of the above applications are all incorporated by reference as if fully set forth herein in their entirety.

FIELD AND BACKGROUND OF THE INVENTION

The present invention, in some embodiments thereof, relates to uses of *Daldinia* sp. or volatile organic compounds derived therefrom.

Plant endophytes are microorganisms that spend most of their life cycle inside plant tissues without causing any visible damage or defense reactions in the host plants. Many endophytes isolated from trees have been found to secrete secondary metabolites ranging from low molecular weight molecules to complex glycoproteins. The secretion of secondary metabolites may help fungi survive in hostile environments. These secondary compounds may help an endophyte to compete with other endophytes for nutrients and space in the plant tissues, and simultaneously benefit the host by protecting it against pathogens. The inner parts of the plant are not hospitable to intruders; in most cases, plants react to invading microorganisms by activating defense systems, including the secretion of, e.g., phenolic compounds, oxidative compounds, enzymes and other substances.

Some species of endophytic fungi have been identified as sources of anticancer, antidiabetic, insecticidal and immunosuppressive compounds. One example of the pharmaceutical use of an endophyte fungus is the anticancer drug paclitexel (Taxol), which was isolated from *Pestalotiopsis microspora*, a fungus that colonizes the Himalayan tree *Taxus wallichiana*.

U.S. Pat. No. 7,267,975 (hereinafter the '975 patent) describes a novel endophytic fungus, which is named *Muscodor vitigenus*, originating from the liana *Paullinia paullinioides*. This fungus produces under certain cultural conditions the well known chemical compound naphthalene, which is used as insect or pest repellent.

U.S. Pat. No. 7,341,862 (hereinafter the '862 patent) describes another novel endophytic fungus, *Muscodor albus*, which produces volatile antibiotics that are effective in the treatment of human and animal waste products. The '862 patent demonstrates that *Muscodor albus* can be used in disposable bags in connection with portable toilets to solve the problem of degradation of waste products in situations where humans are removed from sanitary facilities. The '862 patent describes also non-volatile inhibitors that are produced by *Muscador albus* and that are similarly effective in treating human and animal wastes.

There is an increasing demand in global agriculture, especially in the western world, for natural agents useful for pest control. According to the '975 patent, naphthalene originates from a natural fungus. However, exposure to large amounts of this compound may damage red blood cells, a condition, known as hemolytic anemia. The International Agency for Research on Cancer classifies naphthalene as possibly carcinogenic to humans and animals [Group 2B] stating that hemolytic anemia can occur in children and infants after oral inhalation, exposure or after maternal exposure during pregnancy.

In most cases the preparation and handling of conventional emulsions for pest control, containing toxic pesticides or insecticides, can be harmful to unskilled individuals. Furthermore, some pesticides contain active ingredients that have been shown to act as hormone disruptors in acute and chronic toxicity studies, possibly causing loss of fertility, carcinogenesis, and mutagenesis.

Global widespread application of pesticides on most of the cash crops causes presence of harmful pesticides in the ecosystems, aquifers and surroundings of water systems around the world.

A particular aspect that has received relatively sparse attention is the possible impact of chemical exposure on the fecundity (ability to reproduce) of human populations. In particular, it is known that foods, such as vegetables and fruits, are contaminated with synthetic endocrine disruptors but the extent of the exposure of foods to contaminants and their impact on fecundity in men and women is unknown.

Thus, there is a constant need in the art for unique natural biologically active compounds to be used for biological control. The present invention provides such compounds, originated from an endophytic fungus, which may be used without the risks involved with the exertion of cancer suspect compounds such as naphthalene or other toxic pesticides or insecticides.

Additional background art includes:
U.S. Pat. Nos. 7,754,203, 8,728,462,

SUMMARY OF THE INVENTION

According to an aspect of some embodiments of the present invention there is provided a method of killing a phytopathogen or reducing growth thereof, the method comprising exposing the phytopathogen to an effective amount of a composition comprising a biologically pure culture of *Daldinia* sp. or at least one volatile organic compound (VOC) being produced by the biologically pure culture and capable of killing the phytopathogen or reducing growth thereof.

According to an aspect of some embodiments of the present invention there is provided a method for reducing overall damage to a plant or plant part caused by a phytopathogen, the method comprising exposing the plant or plant part to an effective amount of a composition comprising a biologically pure culture of *Daldinia* sp. or at least one volatile organic compound (VOC) being produced by the biologically pure culture and capable of killing the phytopathogen or reducing growth thereof, thereby reducing overall damage to the plant or plant part.

According to some embodiments of the invention, the plant or plant part is pre-harvested.

According to an aspect of some embodiments of the present invention there is provided a method of storing a plant or plant part, the method comprising exposing a post harvest plant or plant part to an effective amount of a composition comprising a biologically pure culture of *Daldinia* sp. or at least one volatile organic compound (VOC) being produced by the biologically pure culture and capable of killing a phytopathogen or reducing growth thereof, thereby storing the plant or plant part.

According to some embodiments of the invention, the exposing is by immersion, coating, dipping, spraying, evaporation, fogging, scattering, painting on and/or injecting.

According to an aspect of some embodiments of the present invention there is provided a method of producing a volatile organic compound (VOC), the method comprising:
(a) culturing a biologically pure culture of *Daldinia* sp.;
(b) and collecting the volatile composition produced from the strain of *Daldinia* sp.

According to an aspect of some embodiments of the present invention there is provided a composition comprising a pure culture of a *Daldinia* sp. and/or at least one volatile organic compound (VOC) selected from the group consisting of 3-methyl-1-butanol, 2-methyl-1-butanol, 1-methyl-1,3-cyclohexadiene, 1-methyl-1,4-cyclohexadiene, 4-heptanone, isoamyl acetate, 4-heptyn-2-ol, cis-2-octenal, trans-2-octenal, octanal, 4,4-dimethyl-1,3-cyclopentanedione, 2,2,5-trimethylcyclopentanone, phenyl ethyl alcohol, β-elemene, (+)-α-funebrene, α-guaiene, 2-(4-hydroxyphenyl)ethanol, terpenes, α-selinene, β-selinene, α-bulnesene, germacrene A, 7-epi-α-selinene, dauca-4(11),8-diene, veratryl acetone, pogostol, 3-methoxy-2-naphthol and mixtures thereof and an agricultural acceptable carrier.

According to an aspect of some embodiments of the present invention there is provided a composition comprising more than one volatile organic compound (VOC) being produced of a biologically pure culture of *Daldinia* sp.

According to some embodiments of the invention, the VOC comprises 2-10 different VOCs.

According to some embodiments of the invention, the VOC comprises 2-8 different VOCs.

According to some embodiments of the invention, the VOC comprises 2-6 different VOCs.

According to some embodiments of the invention, the VOC comprises 2-4 different VOCs.

According to some embodiments of the invention, the VOC comprises 2-3 different VOCs.

According to some embodiments of the invention, the composition further comprises an agricultural acceptable carrier.

According to some embodiments of the invention, the VOC comprises 3-methyl-1-butanol, (±)-2-methyl-1-butanol, 4-heptanone, and isoamyl acetate.

According to some embodiments of the invention, the 3-methyl-1-butanol, (±)-2-methyl-1-butanol, 4-heptanone, and isoamyl acetate are in a ratio of 1:1:2:1.

According to some embodiments of the invention, the VOC comprises 4-heptanone and trans-2-octenal.

According to some embodiments of the invention, the 4-heptanone and trans-2-octenal are in a ratio of 1:1.

According to an aspect of some embodiments of the present invention there is provided a composition comprising or consisting of 4-heptanone and/or a trans-2-octenal and an agricultural acceptable carrier.

According to some embodiments of the invention, the composition further comprises an agent selected from the group consisting of a fertilizer, an antibiotic a ripening inhibitor and a sprouting inhibitor.

According to some embodiments of the invention, the VOC is selected from the group consisting of 3-methyl-1-butanol, 2-methyl-1-butanol, 1-methyl-1,3-cyclohexadiene, 1-methyl-1,4-cyclohexadiene, 4-heptanone, isoamyl acetate, 4-heptyn-2-ol, cis-2-octenal, trans-2-octenal, octanal, 4,4-dimethyl-1,3-cyclopentanedione, 2,2,5-trimethylcyclopentanone, phenyl ethyl alcohol, β-elemene, (+)-α-funebrene, α-guaiene, 2-(4-hydroxyphenyl)ethanol, terpenes, α-selinene, β-selinene, α-bulnesene, germacrene A, 7-epi-α-selinene, dauca-4(11),8-diene, veratryl acetone, pogostol, 3-methoxy-2-naphthol and mixtures thereof.

According to some embodiments of the invention, the phytopathogen is a microorganism.

According to some embodiments of the invention, the phytopathogen is an insect or an aphid.

According to some embodiments of the invention, the phytopathogen is a nematode.

According to some embodiments of the invention, the phytopathogen is not a nematode.

According to some embodiments of the invention, the nematode is *Meloidogyne javanica*.

According to some embodiments of the invention, the phytopathogen is a mold.

According to some embodiments of the invention, the phytopathogen is a fungus.

According to some embodiments of the invention, the phytopathogen is selected from the group consisting of *Pythium ultimum, Pythium aphanidermatum, Alternaria alternata* pathotype tangelo, *Fusarium oxysporum, Fusarium euwallaceae, Fusarium mangiferae, Coniella* sp., *Phoma tracheiphila, Colletotrichum* sp., *Rhizoctonia solani, Alternaria alternata, Botrytis cinerea, Sclerotinia sclerotiorum, Penicillium digitatum, Lasiodiplodia theobromae, Neoscytalidium dimidiatum* and *Aspergillus niger*.

According to some embodiments of the invention, the nematode is *Meloidogyne javanica*.

According to some embodiments of the invention, the fungus is selected from the group *A. niger, Botrytis cinerea, Alternaria alternata* and *Penicillium digitatum*.

According to some embodiments of the invention, the aphid is selected from the group consisting of *Myzus persicae, Aphis gossypii, Brevicoryne brassicae, Aphis nerii, Bemisia tabaci* and *Rhopalosiphum maidis*.

According to some embodiments of the invention, the storing comprises delaying sprouting.

According to an aspect of some embodiments of the present invention there is provided a surface coated with the composition.

According to an aspect of some embodiments of the present invention there is provided a pharmaceutical or cosmetic composition comprising a VOC being produced by the biologically pure culture of a *Daldinia* sp. and an additive having antibiotic or antimicrobial or sprout-inhibitory activities and additives.

According to some embodiments of the invention, the additive is selected from carriers, colorants, emulsifying agents, fillers, gelling agents, humectants, preservatives, solubilizing agents, surfactants, thickening agents and combinations thereof.

According to some embodiments of the invention, the pharmaceutical or cosmetic composition used for topical or other insect repellent or cosmetic formulations with the addition of additives selected from carriers, colorants, emulsifying agents, fillers, gelling agents, humectants, preservatives, solubilizing agents, surfactants, thickening agents and combinations thereof.

According to some embodiments of the invention, the pharmaceutical or cosmetic composition employed as an attractant in traps to control infestations of insects or pests, thereby preventing or diminishing the pest reproduction in greenhouse environments.

According to some embodiments of the invention, the *Daldinia* sp. comprises *D. concentrica*.

According to some embodiments of the invention, the VOC is a synthetic VOC.

According to some embodiments of the invention, the VOC is purified from a culture of the *Daldinia* sp.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 1:
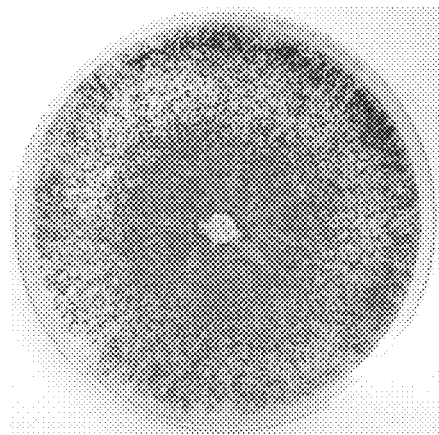
FIG. 1 illustrates the growth of *D. concentrica* on potato dextrose agar (PDA) Petri plates.
Figure 2:
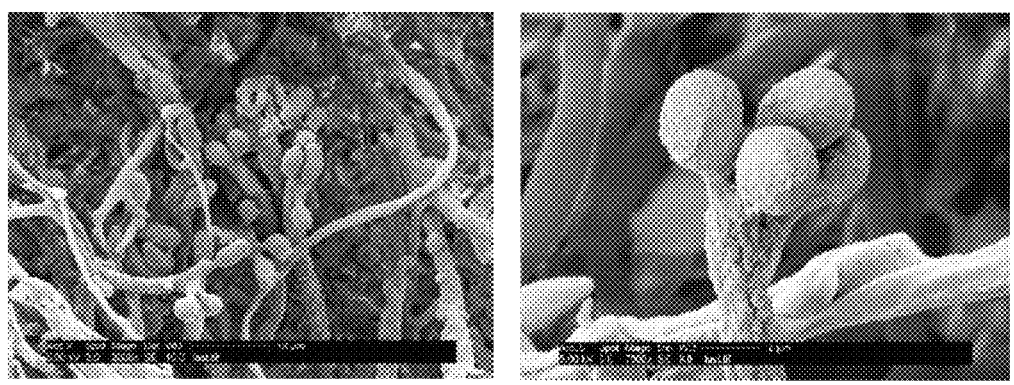
FIG. 2 illustrates the pictures of *D. concentrica* hypha (left) and spores (right) under electron scanning microscope.
Figure 3:
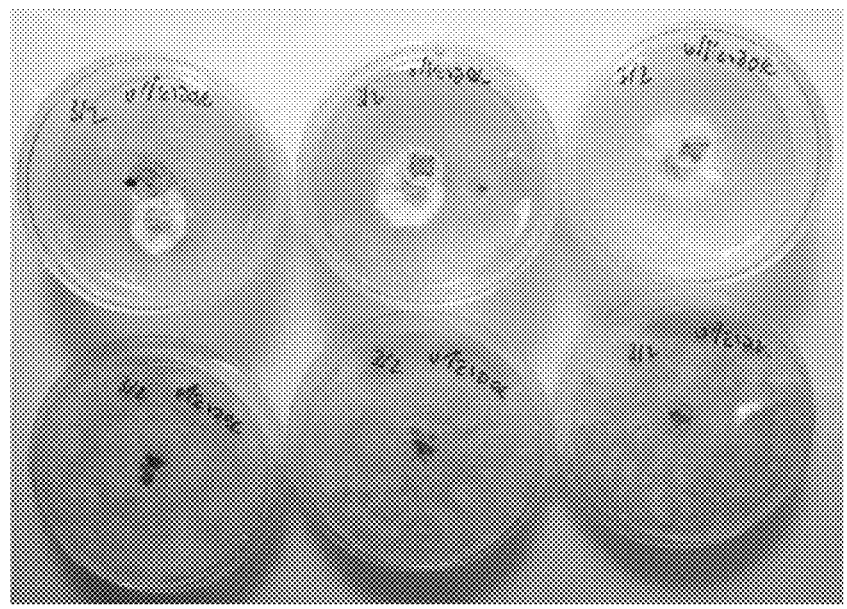

FIG. 3 demonstrates the examination of the antimicrobial activity of *D. concentrica*.

Figure 4:
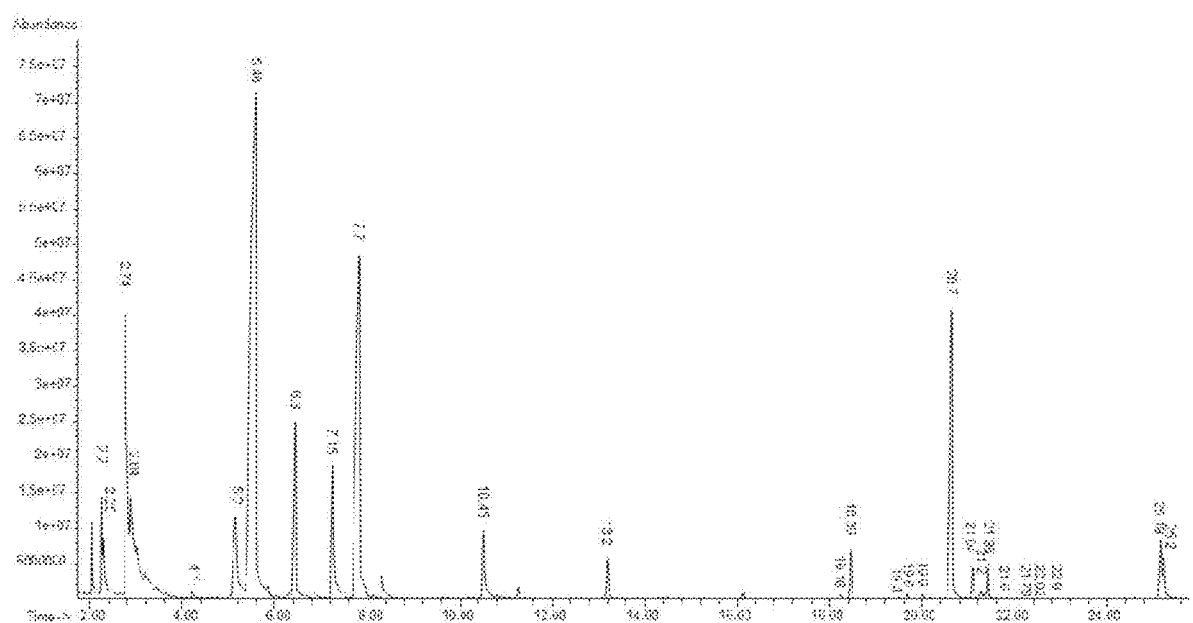

FIG. 4 illustrates the GC/MS chromatogram of the VOCs, detailed in Table 2, emitted by *D. concentrica*.

Figure 5A:
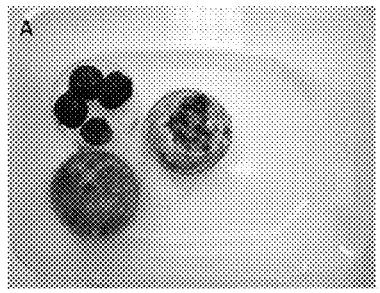
Figure 5B:
Figure 5C:

FIGS. 5A-C demonstrate the effect of the antimicrobial activity of *D. concentrica* on dried apricot, raisin and plum rot causing pathogens.

Figure 6A:
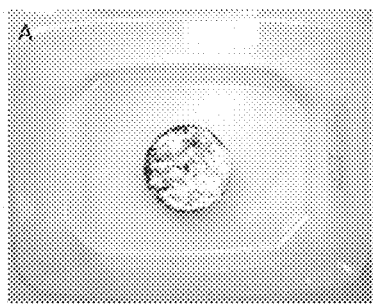
Figure 6B:
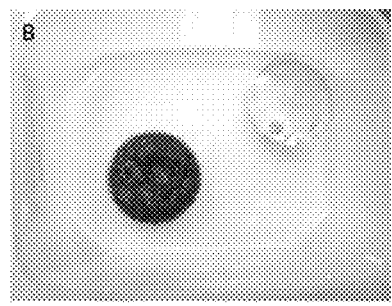
Figure 6C:
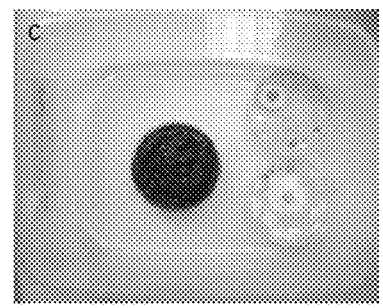

FIGS. 6A-C demonstrate the effect of the antimicrobial activity of *D. concentrica* on commercial tomato paste inoculated with *Penicillium digitatum*.

Figure 7A:
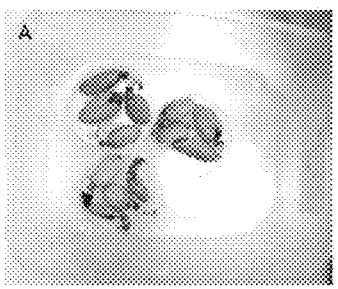
Figure 7B:
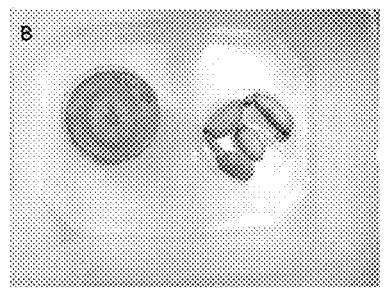
Figure 7C:
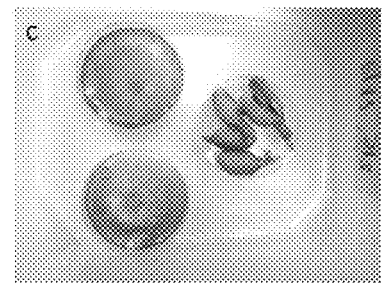

FIGS. 7A-C demonstrate the effect of the antimicrobial activity of *D. concentrica* on peanuts inoculated with *Aspergillus niger*.

FIGS. 8A-D demonstrate the effect of the antimicrobial activity of *D. concentrica* on oranges inoculated with *Penicillium digitatum*.

FIG. 9 demonstrates the effect of the nematicidal) activity of *D. concentrica* on the viability of J2 larvae of the plant pathogenic nematode *Meloidogyne javanica*.

FIG. 10 demonstrates the effect of the antimicrobial activity of "Mixture 4" on the growth of plant pathogenic fungi at various temperatures.

FIG. 11 demonstrates the effect of the antimicrobial activity of "Mixture 21" on the growth of plant pathogenic fungi at various temperatures.

Figure 12:
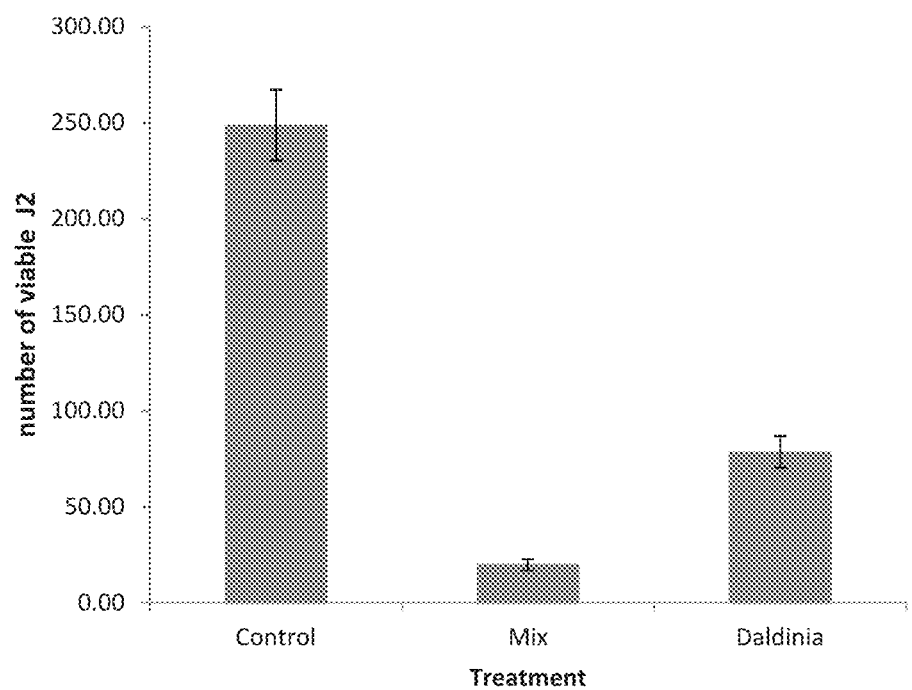

FIG. 12 demonstrates the effect of the nematicidal activity of "Mixture 4" and *D. concentrica* on the viability of J2 larvae of the plant pathogenic nematode *Meloidogyne javanica*.

FIGS. 13A-F demonstrate the effect of the antimicrobial activity of "Mixture 4" on peanut inoculated with *Aspergillus niger* and *Penicillium digitatum*.

Figure 14A:
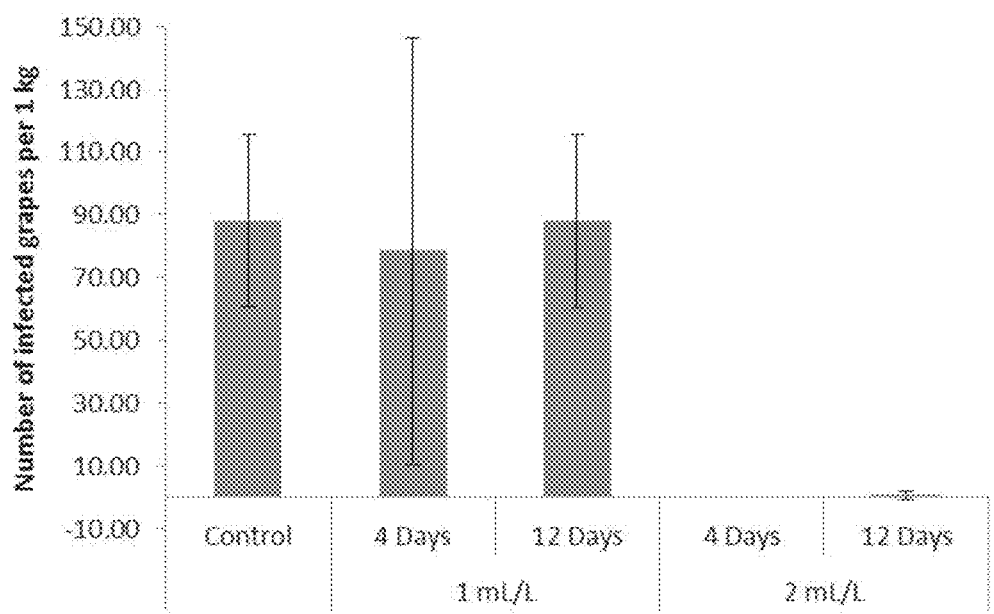
Figure 14B:
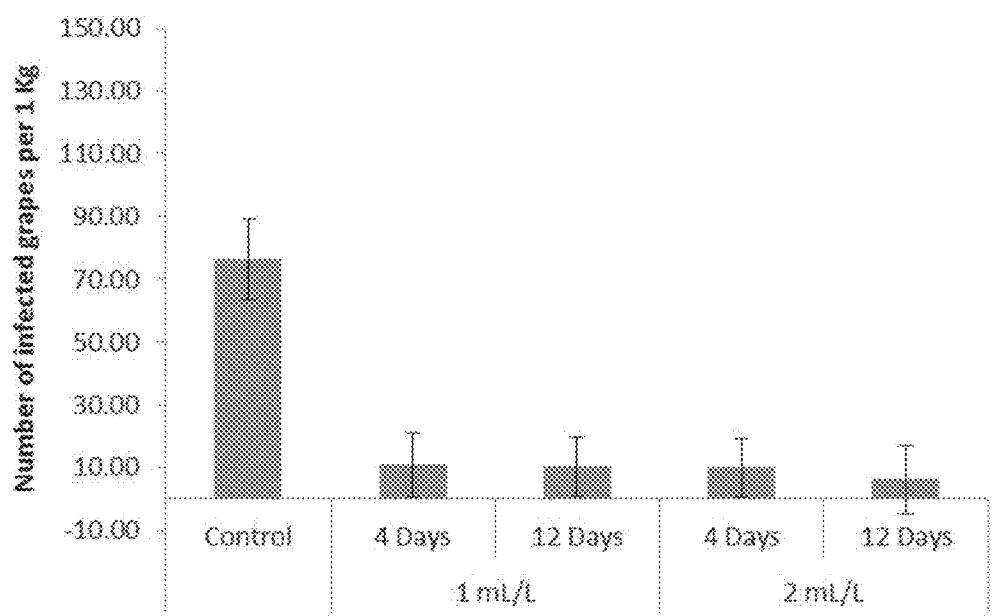

FIGS. 14A-B demonstrate the effect of the antimicrobial activity of "Mixture 4" on disease symptoms of grapes with or without inoculation with *Botrytis cinerea*.

FIGS. 15A-E demonstrate the effect of the antimicrobial activity of "Mixture 4" on wheat grains.

FIGS. 16A-E demonstrate the effect of the antimicrobial activity of "Mixture 4" on oranges inoculated with *Penicillium digitatum*.

FIG. 17 demonstrates the effect of the pesticide activity of "Mixture 21" on various plant aphids.

FIG. 18 demonstrates the effect of the pesticide activity of "Mixture 21" on cucumber plants (*Cucumis sativus*).

FIGS. 19A-E demonstrate the effect of the sprout-inhibitory activity of "Mixture 21" on potato tubers.

FIGS. 20A-D show second stage juveniles' phenotype following exposure to *D. concentrica* culture, synthetic mixture, and the compound 4-heptanone. The nematodes were exposed to each condition for 48 hours at 25° C. in the dark before visualization. FIG. 20A. Control—non treated nematodes. FIG. 20B. Nematodes exposed to three *D. concentrica* culture plates (50 mm in diameter with 5 mL growth medium) pre-grown for 4 days. FIG. 20C. Nematodes exposed to 0.25 mL/L of synthetic mixture preloaded to 125 mg of perlite particles. FIG. 20D. Nematodes exposed to 0.05 mL/L of the compound 4-heptanone preloaded to 25 mg of perlite particles. The bar indicates 500 m.

Figure 21:
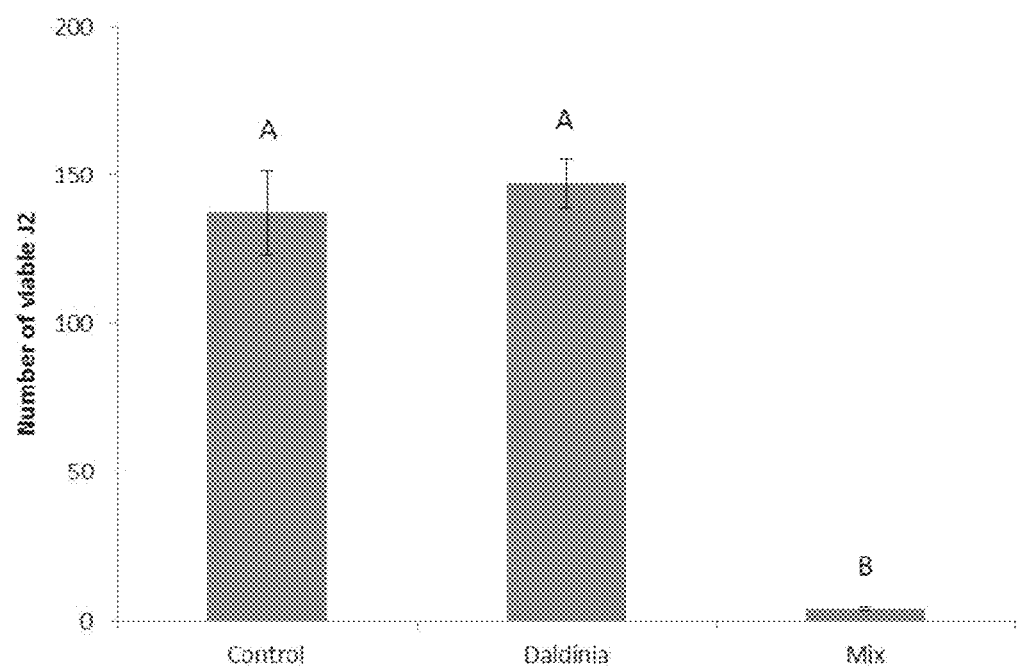

FIG. 21 is a graph showing the effect of *D. concentrica* volatiles and the synthetic mixture on *M. javanica* eggs. The eggs (10 repetitions of 800 eggs per treatment) were exposed to either three *D. concentrica* culture plates (50 mm in diameter with 5 mL growth medium) or to 0.25 mL/L of the mixture preloaded on 125 mg of perlite particles. Only viable *M. javanica* J2 larvae, which hatched from eggs that were exposed for 48 hours to the volatiles, were counted (Average±SE). Different letters above the bars denote a significant difference (P≤0.05, analysis of variance) between samples as analyzed by Tukey-Kramer multiple comparison test. The experiment was repeated three times and similar results were obtained.

Figure 22:
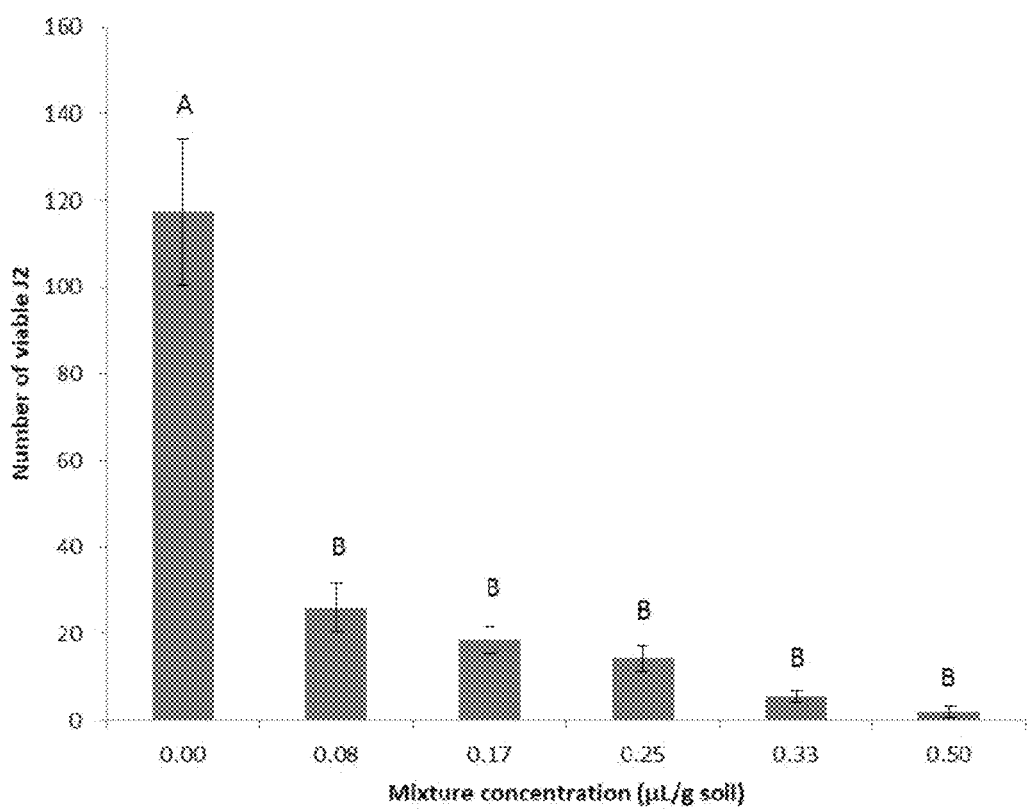

FIG. 22 is a graph showing the activity of the synthetic mixture in loam soil. The nematodes (5 repetitions of 500 J2 larvae in each cup) were mixed into 60 g of soil in sealed 50 mL cups and exposed to increasing concentrations of the mixture for 48 hours before counting the viable J2 larvae (Average±SE). Different letters above the bars denote a significant difference (P≤0.05, analysis of variance) between samples as analyzed by Tukey-Kramer multiple comparison test. The experiment was repeated twice and similar results were obtained.

Figure 23A:
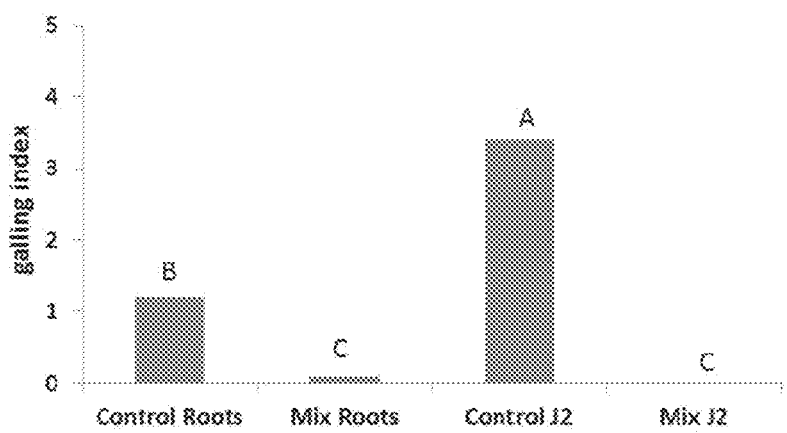
Figure 23B:
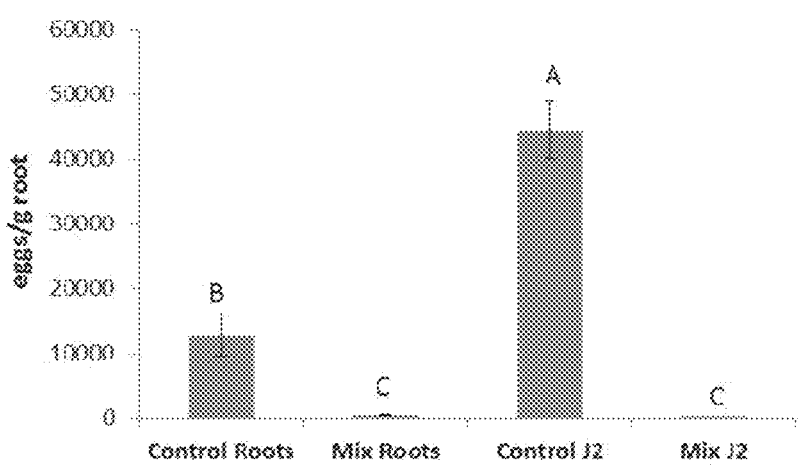
Figure 23C:
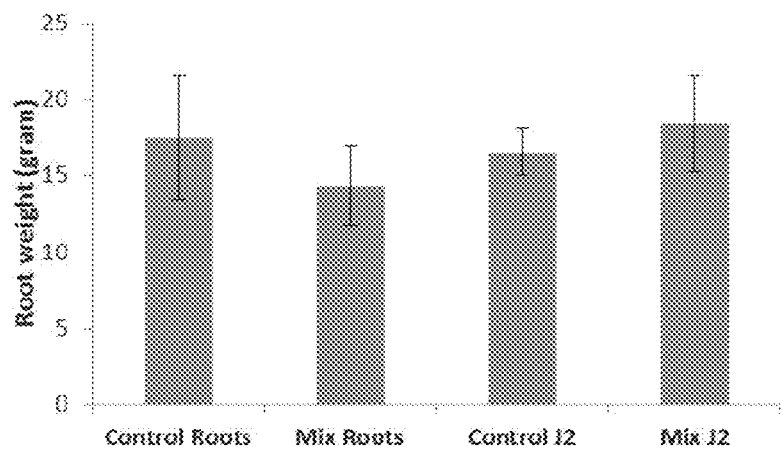

FIGS. 23A-C are graphs showing the effect of the synthetic mixture in greenhouse experiments. Susceptible tomato seedlings were planted in inoculated soil with or without pretreatment with the synthetic mixture. Control roots—soil inoculated with roots inhabited by *M. javanica* (equivalent of 4000 eggs in root suspension in each pot). Mix roots-soil inoculated with roots inhabited by *M. javanica* supplemented with the synthetic mixture. Control J2-soil inoculated by direct addition of *M. javanica* J2 larvae (4000 J2 larvae in each pot). Mix J2-soil inoculated by direct addition of *M. javanica* J2 larvae and supplemented with the synthetic mixture. FIG. 23A. Galling index (averaged of 5 repetitions). Different letters above the bars denote a significant difference (P≤0.05, analysis of variance) between samples as analyzed by Tukey-Kramer multiple comparison test. FIG. 23B. Number of *M. javanica* eggs per gram of root (Average±SE). This effect was statistically significant according to 1-way ANOVA with Tukey-Kramer post-test (F<0.0001). FIG. 23C. Root weight (Average±SE). No significant differences between treatments (p>0.01). The experiment was repeated twice and similar results were obtained.

DESCRIPTION OF SPECIFIC EMBODIMENTS OF THE INVENTION

The present invention, in some embodiments thereof, relates to uses of *Daldinia* sp. or volatile organic compounds derived therefrom.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Without wishing to be bound by any particular theory it is assumed herein that, as it is typical for endophytic fungi, the establishment of this endophytic fungus is not recognized as a threat to the plant and does not induce any visible defense response.

Whilst reducing the present invention to practice, the inventors of the present invention have uncovered that *D. concentrica* is an endophytic, biologically active, fungus. The *D. concentrica* fungus is able to emit in its wild-type form Volatile Organic Compounds (VOCs) which are devoid of naphthalene and it is thus a unique endophytic fungus belonging to a limited group of biologically active VOCs-emitting fungi to be described to date.

It has also been surprisingly discovered by the inventors of the present invention that the VOCs have strong antibiotic activity against other microorganisms, nematodes, aphids, weeds, and other pests, as detailed herein below. The antibiotic activity is concerned with the ability to produce and emit biologically active VOCs that control or inhibit or decimate the growth of other microorganisms.

Thus, according to an aspect of the invention there is provided a method of killing a phytopathogen or reducing growth thereof, the method comprising exposing the phytopathogen to an effective amount of a composition comprising a biologically pure culture of *Daldinia* sp. or at least one volatile organic compound (VOC) being produced by the biologically pure culture (as listed below) and capable of killing the phytopathogen or reducing growth thereof.

According to an additional or an alternative aspect of the invention there is provided a method for reducing overall damage to a plant or plant part caused by a phytopathogen, the method comprising exposing the plant or plant part to an effective amount of a composition comprising a biologically pure culture of *Daldinia* sp. or at least one volatile organic compound (VOC) being produced by the biologically pure culture and capable of killing the phytopathogen or reducing growth thereof, thereby reducing overall damage to the plant or plant part.

According to an additional or an alternative aspect of the invention there is provided a method of storing a plant or plant part, the method comprising exposing a post harvest plant or plant part to an effective amount of a composition comprising a biologically pure culture of *Daldinia* sp. or at least one volatile organic compound (VOC) being produced by the biologically pure culture and capable of killing a phytopathogen or reducing growth thereof, thereby storing the plant or plant part.

As used herein the term "phytopathogen" refers to an organism that is pathogenic to plants.

The phytopathogenic organism refers to a multicellular organism e.g., insects, fungi, animals, nematodes or a microorganism that can cause plant disease, including bacteria, fungi as well as oomycetes, chytrids, algae, and nematodes.

The pathogen may be in any developmental stage. For example contemplated are nematodes at all four molts from the juvenile to the adult phase of their life cycle e.g., including eggs.

According to a specific embodiment, the phytopathogen is a microorganism (e.g., bacteria).

According to a specific embodiment, the phytopathogen is an insect or an aphid.

According to a specific embodiment, the phytopathogen is a nematode.

According to a specific embodiment, the phytopathogen is a fungus (e.g., mold).

Specifically, nematodes that may be controlled using the method set forth above include but are not limited to parasitic nematodes such as root-knot, reniform, cyst, and lesion nematodes, including but not limited to *Aphelenchoides* spp., *Belonolaimus* spp., *Bursaphalenchus* spp., *Criconema* spp. *Globodera* spp., *Meloidogyne* spp., *Tylenchorhynchus* spp., *Helicotylenchus* spp., *Heterodera* spp., *Hoplolaimus* spp., *Pratylenchus* spp., *Rotylenchulus* spp., *Trichodorus* spp., and *Xiphinema* spp. In particular, the parasitic nematodes may include but are not limited to seed gall nematodes (*Afrina wevelli*), bentgrass nematodes (*Anguina agrostis*), shoot gall nematodes (*Anguina* spp.), seed gall nematodes (*Anguina* spp., *A. amsinckiae, A. balsamophila; A. tritici*), fescue leaf gall nematodes (*A. graminis*), ear-cockle (or wheat gall) nematodes (*Anguina tritici*), bud and leaf (or foliar) nematodes (*Aphelenchoides* spp., *A. subtenuis*), begonia leaf (or fern, or spring crimp, or strawberry foliar, or strawberry nematodes, or summer dwarf) nematodes (*A. fragariae*), fern nematodes (*A. olesistus*), rice nematodes (*A. oryzae*), currant nematodes (*A. ribes*), black currant (or chrysanthemum) nematodes (*A. ritzemabosi*), chrysanthemum foliar or leaf nematodes (*A. ritzemabosi*), rice white-tip (or spring dwarf, or strawberry bud) nematodes (*A. besseyi*), fungus-feeding (mushroom) nematodes (*Aphelenchoides composticola*), *Atalodera* spp. (*Atalodera lonicerae, Atalodera ucri*), spine nematodes (*Bakernema variabile*), sting nematodes (*Belonolaimus* spp., *B. gracilis, B. longicaudatus*), pine wood nematodes (*Bursaphalenchus* spp., *B. xylophilus, B. mucronatus*), sessile nematodes (*Cacopaurus* spp., *C. epacris, C. pestis*), amaranth cyst nematodes (*Cactodera amaranthi*), birch cyst nematodes (*C. betulae*), cactus cyst nematodes (*C. cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Criconema* spp., *C. civellae, C. decalineatum, C. spinalineatum*), ring nematodes (*Criconemella axeste, C. curvata, C. macrodora, C. parva*), ring nematodes (*Criconemoides* spp., *C. citri, C. simile*), spine nematodes (*Crossonema fimbriatum*), eucalypt cystoid nematodes (*Cryphodera eucalypti*), bud, stem and bulb nematodes (*Ditylenchus* spp., *D. angustus, D. dipsaci, D. destructor, D. intermedius*), Mushroom spawn nematodes (*D. myceliophagus*), awl nematodes (*Dolichodorus* spp., *D. heterocephalus, D. heterocephalous*), spear nematodes (*Dorylaimus* spp.), stunt nematodes (*Geocenamus superbus*), cyst nematodes (*Globodera* spp.), yarrow cyst nematodes (*G. achilleae*), milfoil cyst nematodes (*G. millefolii*), apple cyst nematodes (*G. mali*), white cyst potato nematodes (*G. pallida*), golden nematodes (*G. rostochiensis*), tobacco cyst nematodes (*G. tabacum*), Osborne's cyst nematodes (*G. tabacum solanacearum*), horsenettle cyst nematodes (*G. tabacum virginiae*), pin nematodes (*Gracilacus* spp., *G. idalimus*), spiral nematodes (*Helicotylenchus* spp., *H. africanus, H. digonicus, H. dihystera, H. erythrinae, H. multicinctus, H. paragirus, H. pseudorobustus, H. solani,*

*H. spicaudatus*), sheathoid nematodes (*Hemicriconemoides* spp., *H. biformis, H. californianus, H. chitwoodi, H. floridensis, H. wessoni*), sheath nematodes (*Hemicycliophora* spp., *H. arenaria, H. biosphaera, H. megalodiscus, H. parvana, H. poranga, H. sheri, H. similis, H. striatula*), cyst nematodes (*Heterodera* spp.), almond cyst nematodes (*H. amygdali*), oat (or cereal) cyst nematodes (*H. avenae*), Cajanus (or pigeon pea) cyst nematodes (*H. cajani*), Bermuda grass (or heart-shaped, or Valentine) cyst nematodes (*H. cardiolata*), carrot cyst nematodes (*H. carotae*), cabbage cyst nematodes or *brassica* root eelworm (*H. cruciferae*), nutgrass (or sedge) cyst nematodes (*H. cyperi*), Japanese cyst nematodes (*H. elachista*), fig (or *ficus*, or rubber) cyst nematodes (*H. fici*), galeopsis cyst nematodes (*H. galeopsidis*), soybean cyst nematodes (*H. glycines*), alfalfa root (or pea cyst) nematodes (*H. goettingiana*), buckwheat cyst nematodes (*H. graduni*), barley cyst nematodes (*H. hordecalis*), hop cyst nematodes (*H. humuli*), Mediterranean cereal (or wheat) cyst nematodes (*H. latipons*), lespedeza cyst nematodes (*H. lespedezae*), Kansas cyst nematodes (*H. longicolla*), cereals root eelworm or oat cyst nematodes (*H. major*), grass cyst nematodes (*H. mani*), lucerne cyst nematodes (*H. medicaginis*), cyperus (or motha) cyst nematodes (*Heterodera mothi*), rice cyst nematodes (*H. oryzae*), Amu-Darya (or camel thorn cyst) nematodes (*H. oxiana*), dock cyst nematodes (*H. rosii*), *rumex* cyst nemtodes (*H. rumicis*), sugar beet cyst nematodes (*H. schachtii*), willow cyst nematodes (*H. salixophila*), knawel cyst nematodes (*H. scleranthii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli, H. caudacrena, H. gracilis, H. oryzae*), lance nematodes (*Hoplolaimus* spp.), Columbia nematodes (*H. columbus*), Cobb's lance nematodes (*H. galeatus*), crown-headed lance nematodes (*H. tylenchiformis*), pseudo root-knot nematodes (*Hypsoperine graminis*), needle nematodes (*Longidorus* spp., *L. africanus, L. sylphus*), ring nematodes (*Macroposthonia* (=Mesocriconema) xenoplax), cystoid nematodes (*Meloidodera* spp.), pine cystoid nematodes (*M. floridensis*), tadzhik cystoid nematodes (*M. tadshikistanica*), cystoid body nematodes (*Meloidoderita* spp.), stunt nematodes (*Merlinius* spp., *M. brevidens, M. conicus, M. grandis, M. microdorus*), root-knot nematodes (*Meloidogyne* spp., *M. acronea, M. arenaria, M. artiellia, M. brevicauda, M. camelliae, M. carolinensis, M. chitwoodi, M. exigua, M. graminicola, M. hapla, M. hispanica, M. incognita, M. incognita acrita, M. indica, M. inornata, M. javanica, M. kikuyuensis, M. konaensis, M. mali, M. microtyla, M. naasi, M. ovalis, M. platani, M. querciana, M. sasseri, M. tadshikistanica, M. thamesi*), knapweed nematodes (*Mesoanguina picridis*), Douglas fir nematodes (*Nacobbodera chitwoodi*), false root-knot nematodes (*Nacobbus aberrans, N. batatiformis, N. dorsalis*), sour paste nematodes (*Panagrellus redivivus*), beer nematodes (*P. silusiae*), needle nematodes (*Paralongidorus microlaimus*), spiral nematodes (*Pararotylenchus* spp.), stubby-root nematodes (*Paratrichodorus allius, P. minor, P. porosus, P. renifer*), pin nematodes (*Paratylenchus* spp., *P. baldaccii, P. bukowinensis, P. curvitatus, P. dianthus, P. elachistus, P. hamatus, P. holdemani, P. italiensis, P. lepidus, P. nanus, P. neoamplycephalus, P. similis*), lesion (or meadow) nematodes (*Pratylenchus* spp., *P. alleni, P. brachyurus, P. coffeae, P. convallariae, P. crenatus, P. flakkensis, P. goodeyi, P. hexincisus, P. leiocephalus, P. minyus, P. musicola, P. neglectus, P. penetrans, P. pratensis, P. scribneri, P. thornei, P. vulnus, P. zeae*), stem gall nematodes (*Pterotylenchus cecidogenus*), grass cyst nematodes (*Punctodera punctate*), stunt nematodes (*Quinisulcius acutus, Q. capitatus*), burrowing nematodes (*Radopholus* spp.), banana-root nematodes (*R. similis*), rice-root nematodes (*R. oryzae*), red ring (or coconut, or cocopalm) nematodes (*Rhadinaphelenchus cocophilus*), reniform nematodes (*Rotylenchulus* spp., *R. reniformis, R. parvus*), spiral nematodes (*Rotylenchus* spp., *R. buxophilus, R. christiei, R. robustus*), Thorne's lance nematodes (*R. uniformis*), *Sarisodera hydrophylla*, spiral nematodes (*Scutellonema* spp., *S. blaberum, S. brachyurum, S. bradys, S. clathricaudatum, S. christiei, S. conicephalum*), grass root-gall nematodes (*Subanguina radicicola*), round cystoid nematodes (*Thecavermiculatus andinus*), stubby-root nematodes (*Trichodorus* spp., *T. christiei, T. kurumeensis, T. pachydermis, T. primitivus*), vinegar eels (or nematodes) (*Turbatrix aceti*), stunt (or stylet) nematodes (*Tylenchorhynchus* spp., *T. agri, T. annulatus, T. aspericutis, T. claytoni, T. ebriensis, T. elegans, T. golden, T. graciliformis, T. martini, T. mashhoodi, T. microconus, T. nudus, T. oleraceae, T. penniseti, T. punensis*), citrus nematodes (*Tylenchulus semipenetrans*), dagger nematodes (*Xiphinema* spp., *X. americanum, X. bakeri, X. brasiliense, X. brevicolle, X. chambersi, X. coxi, X. diversicaudatum X. index, X. insigne, X. nigeriense, X. radicicola, X. setariae, X. vulgarae, X. vuittenezi*). In a particular embodiment nematodes controlled are member of the *Meloidogyne* spp, particularly, *M. hapla* or *M. incognita*.

Phytopathogenic insects controlled by the method set forth above include but are not limited to non-Culicidae larvae insects from the order (a) *Lepidoptera*, for example, *Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiella, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.; (b) *Coleoptera*, for example, *Agriotes* spp., *Alphitobius* sp., *Anomola* spp., e.g., *Anomala orientalis, Anthonomus* spp., *Atomaria linearis, Chaetocnema tibialis, Cosmopolites* spp., *Curculio* spp., *Cyclocephala* spp., e.g., *Cyclocephala lurida, Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Otiorhynchus sulcatus, Phlyctinus* spp., *Popillia* spp., e.g., *Popilla japonica, Psylliodes* spp., *Rhizopertha* spp., e.g., *Rhizotrogus majalis, Sitophilus* spp., *Sitotroga* spp., *Tenebrio* spp., *Tribolium* spp. and *Trogoderma* spp.; (c) *Orthoptera*, for example, *Blatta* spp., *Blattella* spp., *Gryllotalpa* spp., *Leucophaea maderae, Locusta* spp., *Periplaneta* spp. and *Schistocerca* spp.; (d) *Isoptera*, for example, *Reticulitermes* spp.; (e) *Psocoptera*, for example, *Liposcelis* spp.; (f) *Anoplura*, for example, *Haematopinus* spp., *Linognathus* spp., *Pedicu-*

*lus* spp., *Pemphigus* spp. and *Phylloxera* spp.; (g) *Mallophaga*, for example, *Damalinea* spp. and *Trichodectes* spp.; (h) *Thysanoptera*, for example, *Frankliniella* spp., *Hercinotnrips* spp., *Taeniothrips* spp., *Thrips palmi*, *Thrips tabaci* and *Scirtothrips aurantii*; (i) *Hemiptera*, for example, *Cimex* spp., *Distantiella theobroma*, *Dysdercus* spp., *Euchistus* spp., *Eurygaster* spp., *Leptocorisa* spp., *Nezara* spp., *Piesma* spp., *Rhodnius* spp., *Sahlbergella singularis*, *Scotinophara* spp. and *Tniatoma* spp.; *Aleurothrixus floccosus*, *Aleyrodes brassicae*, *Aonidiella* spp., *Aphididae*, *Aphis* spp., *Aspidiotus* spp., *Bactericera* spp., *Bemisia tabaci*, *Ceroplaster* spp., *Chrysomphalus aonidium*, *Chrysomphalus dictyospermi*, *Coccus hesperidum*, *Empoasca* spp., *Eriosoma larigerum*, *Erythroneura* spp., *Gascardia* spp., *Laodelphax* spp., *Lecanium corni*, *Lepidosaphes* spp., *Macrosiphus* spp., *Myzus* spp., *Nephotettix* spp., *Nilaparvata* spp., *Paratoria* spp., *Pemphigus* spp., *Planococcus* spp., *Pseudaulacaspis* spp., *Pseudococcus* spp., *Psylla* spp., *Pulvinaria aethiopica*, *Quadraspidiotus* spp., *Rhopalosiphum* spp., *Saissetia* spp., *Scaphoideus* spp., *Schizaphis* spp., *Sitobion* spp., *Trialeurodes vaporariorum*, *Triozidae* spp., *Trioza erytreae* and *Unaspis citri*; (j) *Hymenoptera*, for example, *Acromyrmex*, *Atta* spp., *Cephus* spp., *Diprion* spp., *Diprionidae*, *Gilpinia polytoma*, *Hoplocampa* spp., *Lasius* spp., *Monomorium pharaonic*, *Neodiprion* spp., *Solenopsis* spp. and *Vespa* spp.; (k) *Diptera*, for example, *Aedes* spp., *Antherigona soccata*, *Bibio hortulanus*, *Calliphora erythrocephala*, *Ceratitis* spp., *Chrysomyia* spp., *Cuterebra* spp., *Dacus* spp., *Delia* spp., *Delia radicum*, *Drosophila* spp., e.g., *Drosophila suzukii*; *Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis pomonella*, *Sciara* spp., *Stomoxys* spp., *Tabanus* spp., *Tannia* spp. and *Tipula* spp.; (l) *Siphonaptera*, for example, *Ceratophyllus* spp. and *Xenopsylla cheopis*; (m) from the order Thysanura, for example, *Lepisma saccharina*.

Phytopathogenic bacteria include but are not limited to *Agrobacterium* spp. (e.g., *Agrobacterium tumefaciens*); *Erwinia*, *Pantoea*, *Pectobacterium*, *Serratia*, *S. marcescens*, *Acidovorax*, *Pseudomonas*, *Ralstonia*, *Rhizobacter*, *Rhizomonas*, *Xanthomonas*, *Xylophilus*, *Agrobacterium*, *Rhizobium*, *Bacillus*, *Clostridium*, *Arthrobacter*, *Clavibacter*, *Curtobacterium*, *Leifsonia*, *Rhodococcus*, *Streptomyces*, *Xanthomonas* spp. (*Xanthomonas axonopodis*, *Xanthomonas oryzae* pv. *oryzae*, *Xanthomonas vesicatoria*). In a particular embodiment, phytopathogenic bacteria includes but is not limited to *Clavibacter* spp., *Xanthomonas* spp., *Pseudomonas* (e.g., *Pseudomonas syringae*), *Pectobacterium* (e.g., *Pectobacterium carotovorum*).

Phytopathogenic fungi include but are not limited to *Alternaria* spp. (e.g., *Alternaria alternata*, *Alternaria solani*); *Aphanomyces* spp. (e.g., *Aphanomyces euteiches*); *Aspergillus* spp. (e.g., *Aspergillus niger*, *Aspergillus fumigatus*); *Athelia* spp. (e.g., *Athelia rolfsii*); *Aureobasidium* spp. (e.g., *Aureobasidium pullulans*); *Bipolaris* spp. (e.g. *Bipolaris zeicola*, *Bipolaris maydis*); *Botrytis* spp. (e.g., *Botrytis cinerea*); *Calonectria* spp. (e.g., *Calonectria kyotensis*); *Cephalosporium* spp. (e.g., *Cephalosporium maydis*); *Cercospora* spp. (e.g., *Cercospora medicaginis*, *Cercospora sojina*, *Colletotrichum coccodes*, *Colletotrichum fragariae*, *Colletotrichum graminicola*); *Coniella* spp. (e.g., *Coniella diplodiella*); *Coprinopsis* spp. (e.g., *Coprinopsis psychromorbida*); *Corynespora* spp. (e.g., *Corynespora cassiicola*; *Curvularia* spp. (e.g., *Curvularia pallescens*); *Cylindrocladium* spp. (e.g., *Cylindrocladium crotalariae*); *Diplocarpon* spp. (e.g., *Diplocarpon earlianum*); *Diplodia* spp. (e.g., *Diplodia gossyina*); *Epicoccum* spp. (e.g., *Epicoccum nigrum*); *Erysiphe* spp. (*Erysiphe cichoracearum*); *Fusarium* spp. (e.g., *Fusarium graminearum*, *Fusarium oxysporum* f. sp. *fragariae*, *Fusarium oxysporum* f. sp. *tuberosi*, *Fusarium proliferatum* var. *proliferatum*, *Fusarium solani*, *Fusarium verticillioides*); *Ganoderma* spp. (e.g., *Ganoderma boninense*); *Geotrichum* spp. (e.g., *Geotrichum candidum*); *Glomerella* spp. (e.g., *Glomerella tucumanensis*); *Guignardia* spp. (e.g., *Guignardia bidwellii*); *Kabatiella* spp. (e.g., *Kabatiella zeae*); *Leptosphaerulina* spp. (e.g., *Leptosphaerulina briosiana*); *Leptotrochila* spp. (e.g., *Leptotrochila rnedicaginis*); *Macrophomina* spp. (e.g., *Macrophomina phaseolina*); *Magnaporthe* spp. (e.g., *Magnaporthe grisea*, *Magnaporthe oryzae*); *Microsphaera* spp. (e.g., *Microsphaera manshurica*); *Monilinia* spp. (e.g., *Monilinia fructicola*); *Mucor* spp.; *Mycosphaerella* spp. (e.g., *Mycosphaerella juiensis*, *Mycosphaerella fragariae*); *Nigrospora* spp. (e.g., *Nigrospora oryzae*); *Ophiostoma* spp. (e.g., *Ophiostoma ulmi*); *Penicillium* spp.; *Peronospora* spp. (e.g., *Peronospora manshurica*); *Phakopsora* (e.g., *Phakopsora pachyrhizi*); *Phoma* spp. (e.g., *Phoma foveata*, *Phoma medicaginis*); *Phomopsis* spp (e.g. *Phomopsis longicolla*); *Phytophthora* spp. (e.g., *Phytophthora cinnamomi*, *Phytophthora erythroseptica*, *Phytophthora fragariae*, *Phytophthora infestans*, *Phytophthora medicaginis*, *Phytophthora megasperma*, *Phytophthora palmivora*); *Podosphaera* (e.g., *Podosphaera leucotricha*); *Pseudopeziza* spp. (e.g., *Pseudopeziza medicaginis*); *Puccinia* spp. (e.g., *Puccinia graminis* subsp. *tritici* (UG99), *Puccinia striiformis*, *Puccinia recodita*, *Puccinia sorghi*); *Pyricularia* spp. (*Pyricularia grisea*, *Pyricularia oryzae*); *Pythium* spp. (e.g., *Pythium ultimum*); *Rhizoctonia* spp. (e.g., *Rhizoctonia solani*, *Rhizoctonia zeae*); *Rosellinia* spp., *Sclerotinia* spp. (e.g., *Sclerotinia minor*; *Sclerotinia sclerotiorum*, *Sclerotinina trifoliorum*); *Sclerotium* spp. (e.g., *Sclerotium rolfsii*); *Septoria* spp. (e.g., *Septoria glycines*, *Septoria lycoperski*); *Setomelanomma* spp. (e.g., *Setomelanomma turcica*); *Sphaerotheca* spp. (e.g., *Sphaerotheca macularis*); *Spongospora* spp. (e.g., *Spongospora subterranean*); *Stemphylium* spp., *Synchytrium* spp. (e.g., *Synchytrium endobioticum*), *Verticillium* spp. (e.g., *Verticillium albo-atrum*, *Verticillium dahliae*). In a particular embodiment, the fungus is a member of the *Botrytis* spp. (e.g., *Botrytis cinerea*), *Sclerotinia* spp. (*Sclerotinia minor*), *Sclerotium* spp. (e.g., *Sclerotium rolfsii*), *Macrophomina* spp. (e.g., *Macrophomina phaseolina*), *Verticillium* spp. (e.g., *Verticillium dahliae*), *Fusarium* spp. (e.g., *Fusarium oxysporum* f sp. *fragariae*), *Rhizoctonia* spp. (e.g., *Rhizoctonia solani*), *Pythium* spp. (e.g., *Pythium ultimum*).

According to a specific embodiment, the nematode is of the *M. javanica* species.

According to a specific embodiment, the nematode is not of the *M. javanica* species.

According to a specific embodiment, the phytopathogen is selected from the group consisting of *Pythium ultimum*, *Pythium aphanidermatum*, *Altemaria altemata* pathotype tangelo, *Fusarium oxysporum*, *Fusarium euwallaceae*, *Fusarium mangiferae*, *Coniella* sp., *Phoma tracheiphila*, *Colletotrichum* sp., *Rhizoctonia solani*, *Alternaria alternata*, *Botrytis cinerea*, *Sclerotinia sclerotiorum*, *Penicillium digitatum*, *Lasiodiplodia theobromae*, *Neoscytalidium dimidiatum* and *Aspergillus niger*.

According to a specific embodiment, the fungus is selected from the group *A. niger*, *Botrytis cinerea*, *Altemaria alternata* and *Penicillium digitatum*.

According to a specific embodiment, the aphid is selected from the group consisting of *Myzus persicae, Aphis gossypii, Brevicoryne brassicae, Aphis nerii, Bemisia tabaci* and *Rhopalosiphum maidis*.

As used herein the term "reducing" refers to at least 20%, 30%, 40%, 50%, 60%, 70%, 80% 90% or more, reduction of growth or even 100% arrest of growth in a given time as compared to the growth in that given time of the phytopathogen not being exposed to the treatment as described herein.

The effect of the compositions of the invention may also be described as pesticidal or pestistatic.

As used herein, the term "endophyte" refers to an organism capable of living within a plant or is otherwise associated therewith, and does not cause disease or harm the plant otherwise (i.e. is capable of living symbiotically with the plant). Endophytes can occupy the intracellular or extracellular spaces of plant tissue, including the leaves, stems, flowers, fruits, seeds, or roots. An endophyte can be for example a bacterial or fungal organism.

As used herein "*Daldinia* sp." refers to an endophyte of a genus of fungi in the family Xylariaceae. The endophyte may be of a wild-type form or genetically modified using genetic engineering.

Various species are known in the *Daldinia* genus and these include, but are not limited to, *D. angolensis, D. bakeri, D. bambusicola, D. brachysperma, D. caldariorum, D. childiae, D. clavata, D. concentrica, D. cudonia, D. cuprea, D. dennisii, D. eschscholzii, D. fissa, D. gelatinosa, D. graminis, D. grandis, D. lloydii, D. loculata, D. macrospora, D. mexicana, D. novae-zelandiae, D. occidentalis, D. petriniae, D. placentiformis, D. sacchari, D. simulans, D. singularis, D. vernicosa*.

According to a specific embodiment, the *Daldinia* sp. is *Daldinia concentrica*.

According to an exemplary embodiment, a *Daldinia concentrica* species shares at least 99% identity with each of at least 2 genes (e.g., ITS 5.8S rDNA region and the actin gene, SEQ ID NOs: 1 and 2) e.g., of the strain deposited on Jun. 23, 2008 under the Budapest Treaty in CBS culture collection in the protected cultures section under CBS123047 *Daldinia* sp. OBROB1A.—The culture is characterized by strong, sweet and fruity odor.

As used herein the phrase "biologically pure culture" refers to a culture of the fungus, wherein at least 80% (e.g., at least 85%, 90%, 95%, or even all 100%) of the microorganisms in the culture and even in the composition are of a *Daldinia* sp.

According to a specific embodiment, the composition comprises a single *Daldinia* species.

According to a specific embodiment, the composition comprises two *Daldinia* species.

According to a specific embodiment, the composition comprises two species e.g., *Daldinia* species and another species, which is not a *Daldinia* species (e.g., as further described hereinbelow, in such cases 2 or three biologically pure cultures are combined).

A biologically pure culture is also referred to as "an isolate".

The term "isolated" is intended to specifically refer to an organism (e.g., *Daldinia* sp.) that is removed from its original source and purified from additional components with which it was originally associated. For example, an endophyte may be considered isolated from removed and purified from a plant or plant element so that it is isolated and no longer associated with its source plant or plant element. It should be noted that the composition may include whole *Daldinia* cells, parts thereof and extracts therefrom.

The endophyte may be present as a spore, a hypha, or a mycelia.

In one embodiment, the endophyte is stored such that it is propagatable and can emit the VOCs effective for killing the phytopathogen or reducing growth thereof. For example, the endophyte may be dried (e.g. freeze-dried) or frozen. In another embodiment, the endophyte is in a culture. Media for propagating the endophyte may be selected from the group consisting of: soil, hydroponic apparatus, and/or artificial growth medium. For example for *Daldinia* sp. PDA, PDB, grains as maize (for long term storage), wheat and rice.

Compositions may comprise whole broth cultures, liquid or solid cultures, or suspensions of a *Daldinia* strain, specifically a *Daldinia* sp. strain having at least one of the identifying characteristics of a *Daldinia concentrica* strain, as well as supernatant, filtrate and/or extract or one or more and more particularly a plurality of (i) metabolites, (ii) isolated compounds (iii) volatiles derived from *Daldinia concentrica* strain or (iv) synthetic VOC(s) or derivatives of same having the activity of killing the phytopathogen or reducing the growth thereof.

The emitted VOCs of *D. concentrica* were analyzed by GC/MS technique, as depicted in FIG. 4. These compounds were initially identified by comparing their relative retention indices and mass spectra with those found in the Wiley8, Nist9, HC2205, and KI databases. The identification by GC/MS of selected compounds with the highest biological activity, emitted by *D. concentrica*, was confirmed by employing authentic standards. Table A below provides examples of VOCs which can be used along the teachings of the invention.

TABLE A

| Retention time (Rt), minutes | Emitted VOC | Molecular formula |
|---|---|---|
| 2.2 | 3-methyl-1-butanol | $C_5H_{12}O$ |
| 2.25 | 2-methyl-1-butanol | $C_5H_{12}O$ |
| 2.74 | 1-methyl-1,3-cyclohexadiene | $C_7H_{10}$ |
| 2.84 | 1-methyl-1,4-cyclohexadiene | $C_7H_{10}$ |
| 4.1 | 4-heptanone | $C_7H_{14}O$ |
| 4.33 | Isoamyl acetate | $C_7H_{14}O_2$ |
| 5.2 | 4-heptyn-2-ol | $C_7H_{12}O$ |
| 5.46 | Cis-2-octenal | $C_8H_{14}O$ |
| 6.3 | Octanal | $C_8H_{16}O$ |
| 7.15 | 4,4-dimethyl-1,3-cyclopentanedione | $C_7H_{10}O_2$ |
| 7.7 | 2,2,5-trimethylcyclopentanone | $C_8H_{14}O$ |
| 10.45 | Phenyl ethyl alcohol | $C_8H_{10}O$ |
| 13.2 | undefined alcohol | |
| 18.16 | β-elemene | $C_{15}H_{24}$ |
| 18.39 | β-elemene | $C_{15}H_{24}$ |
| 19.4 | (+)-α-funebrene | $C_{15}H_{24}$ |
| 19.6 | α-guaiene | $C_{15}H_{24}$ |
| 19.9 | 2-(4-hydroxyphenyl)ethanol | $C_8H_{10}O_2$ |
| 20.7 | Terpenes | $C_{10}H_{10}O_3$ |
| 21.04 | β-selinene | $C_{15}H_{24}$ |
| 21.2 | α-selinene | $C_{15}H_{24}$ |
| 21.35 | α-bulnesene | $C_{15}H_{24}$ |
| 21.6 | Gennacrene A | $C_{15}H_{24}$ |
| 21.79 | 7-epi-α-selinene | $C_{15}H_{24}$ |
| 22.02 | Dauca-4(11),8-diene | $C_{15}H_{24}$ |
| 22.9 | Veratryl acetone | $C_{11}H_{14}O_3$ |
| 25.19 | Pogostol | $C_{15}H_{26}O$ |
| 25.2 | 3-methoxy-2-naphthol | $C_{11}H_{10}O_2$ |

According to a specific embodiment, the composition is devoid of naphthalene.

According to a specific embodiment, the composition comprises a pure culture of a *Daldinia* sp. and/or at least one volatile organic compound (VOC) selected from the group consisting of 3-methyl-1-butanol, 2-methyl-1-butanol, 1-methyl-1,3-cyclohexadiene, 1-methyl-1,4-cyclohexadiene, 4-heptanone, isoamyl acetate, 4-heptyn-2-ol, cis-2-octenal, trans-2-octenal, octanal, 4,4-dimethyl-1,3-cyclopentanedione, 2,2,5-trimethylcyclopentanone, phenyl ethyl alcohol, β-elemene, (+)-α-funebrene, α-guaiene, 2-(4-hydroxyphenyl)ethanol, terpenes, α-selinene, β-selinene, α-bulnesene, germacrene A, 7-epi-α-selinene, dauca-4(11),8-diene, veratryl acetone, pogostol, 3-methoxy-2-naphthol and mixtures thereof and an agricultural acceptable carrier.

According to a specific embodiment, the composition comprises a pure culture of a *Daldinia* sp. and/or at least one volatile organic compound (VOC) selected from the group consisting of 3-methyl-1-butanol, 2-methyl-1-butanol, 1-methyl-1,3-cyclohexadiene, 4-heptanone, isoamyl acetate, 4-heptyn-2-ol, cis-2-octenal, trans-2-octenal, octanal, 4,4-dimethyl-1,3-cyclopentanedione, 2,2,5-trimethylcyclopentanone, β-elemene, (+)-α-funebrene, α-guaiene, 2-(4-hydroxyphenyl)ethanol, terpenes, α-selinene, β-selinene, α-bulnesene, germacrene A, 7-epi-α-selinene, dauca-4(11),8-diene, veratryl acetone, pogostol and mixtures thereof and an agricultural acceptable carrier.

According to a specific embodiment, the composition comprises more than one volatile organic compound (VOC) being produced of a biologically pure culture of *Daldinia* sp.

According to a specific embodiment, the composition comprises the VOC comprises 2-10 different VOCs.

According to a specific embodiment, the composition comprises the VOC comprises 2-8 different VOCs.

According to a specific embodiment, the composition comprises the VOC comprises 2-6 different VOCs.

According to a specific embodiment, the composition comprises the VOC comprises 2-4 different VOCs.

According to a specific embodiment, the composition comprises the VOC comprises 2-3 different VOCs.

According to a specific embodiment, the composition comprises the VOC comprises 3-methyl-1-butanol, (±)-2-methyl-1-butanol, 4-heptanone, and isoamyl acetate.

According to a specific embodiment, the composition comprises the 3-methyl-1-butanol, (±)-2-methyl-1-butanol, 4-heptanone, and isoamyl acetate are in a ratio of 1:1:2:1.

According to a specific embodiment, the composition comprises the VOC comprises 4-heptanone and trans-2-octenal.

According to a specific embodiment, the composition comprises the 4-heptanone and trans-2-octenal are in a ratio of 1:1.

According to a specific embodiment, the composition comprises 4-heptanone (e.g., at least 50%, 60%, 70%, 80%, 90%, 100%) and/or a trans-2-octenal (e.g., at least 50%, 60%, 70%, 80%, 90%, 100%) and an agricultural acceptable carrier.

According to a specific embodiment, the composition comprising a VOC is selected from the group consisting of 3-methyl-1-butanol, 2-methyl-1-butanol, 1-methyl-1,3-cyclohexadiene, 1-methyl-1,4-cyclohexadiene, 4-heptanone, isoamyl acetate, 4-heptyn-2-ol, cis-2-octenal, trans-2-octenal, octanal, 4,4-dimethyl-1,3-cyclopentanedione, 2,2,5-trimethylcyclopentanone, phenyl ethyl alcohol, β-elemene, (+)-α-funebrene, α-guaiene, 2-(4-hydroxyphenyl)ethanol, terpenes, α-selinene, β-selinene, α-bulnesene, germacrene A, 7-epi-α-selinene, dauca-4(11),8-diene, veratryl acetone, pogostol, 3-methoxy-2-naphthol and mixtures thereof.

According to the present invention, emitted VOCs referred to as "Mixture 4" comprise 3-methyl-1-butanol, (±)-2-methyl-1-butanol, 4-heptanone, and isoamyl acetate in a ratio of 1:1:2:1.

According to the present invention, emitted VOCs referred to as "Mixture 21" comprise 4-heptanone and trans-2-octenal in a ratio of 1:1.

Trans-2-octenal is interchangeable with cis-2-octenal. The VOC in the composition may be produced by the *Daldinia* strain or may be produced from synthetic compounds, which are available by commercial vendors e.g., Sigma.

Thus, the VOCs in the composition may be a reconstituted mixture of products produced by the strain or may be an artificial mixture of volatile organic compounds.

When natural sources of the compositions of the invention are contemplated the VOCs may be recovered from a *Daldinia* (e.g., *Daldinia concentrica*) culture.

Thus, according to an aspect of the invention there is provided a method of producing a volatile organic compound (VOC), the method comprising:
  (a) culturing a biologically pure culture of *Daldinia* sp.;
  (b) and collecting the volatile composition produced from the strain of *Daldinia* sp.

Thus, the composition of the present invention may be produced by growing the *Daldinia* strain in a liquid medium or on agar plates. The liquid medium may be any suitable liquid nutrient medium comprising carbon and nitrogen sources and inorganic salts. Suitable liquid media are available or may be available from commercial sources or prepared according to published compositions e.g., potato dextrose broth (PDB). In a particular embodiment, the *Daldinia* strain may be grown on a potato dextrose agar (PDA).

Once produced by the *Daldinia*, several methods can be used to isolate/collect/recover the VOCs from the culture media or from vapor in a growth chamber. For example, common separation techniques can be used to remove the cells from the broth or agar, and common isolation procedures, such as (without limitation) extraction, distillation, and carbocolumn trap procedures, can be used to obtain VOCs from the cell-free broth or agar. See, for example, U.S. Pat. Nos. 4,275,234, 5,510,526; 5,641,406, and 5,831,122, and International Patent Application Number WO 93/00440, each of which is hereby incorporated by reference in its entirety.

Fractional distillation and/or absorption chromatography are also non-limiting examples of methods to extract the desired product produced by the *Daldinia* isolates of the present invention. Fractional distillation is the separation of a mixture into its component parts, or fractions, such as in separating chemical compounds by their boiling point by heating them to a temperature at which several fractions of the compound will evaporate. Absorption chromatography is a physical separation method in which the components of a mixture are separated by differences in their distribution between two phases, one of which is stationary (stationary phase) while the other (the mobile phase) moves through it in a definite direction. The substances must interact with the stationary phase to be retained and separated by it.

Gas chromatography is a well known technique for fractionating and determining the relative amounts of various components in a sample containing a mixture of compounds of differing volatilities. For example, the sample is vaporized and the entire resulting quantity of gases is passed through an analytical chromatography column. Chromatographic processes such as gas chromatography can rapidly determine the volatiles content of a multicomponent sample, such as would be produced by the fungal isolates of the present invention.

In some instances, Pressure Swing Adsorption (PSA) may be used to separate some gas species from a mixture of gases under pressure according to the species' molecular characteristics and affinity for an adsorbent material. It operates at near-ambient temperatures and so differs from cryogenic distillation techniques of gas separation. Special adsorptive materials (e.g., zeolites) are used as a molecular sieve, preferentially adsorbing the target gas species at high pressure. The process then swings to low pressure to desorb the adsorbent material.

The composition may be combined or used with another microorganism and/or pesticide (e.g., nematicide, bactericide, fungicide, insecticide). The microorganism may include but is not limited to *Bacillus* spp., *Paecilomyces* spp., *Pasteuria* spp. *Pseudomonas* spp., *Brevabacillus* spp., *Lecanicillium* spp., non-*Ampelomyces* spp., *Pseudozyma* spp., *Streptomyces* spp, *Burkholderia* spp, *Trichoderma* spp, *Gliocladium* spp. or *Muscodor* spp. Alternatively, the agent may be a natural oil or oil-product having nematicidal, fungicidal, bactericidal and/or insecticidal activity (e.g., paraffinic oil, tea tree oil, lemongrass oil, clove oil, cinnamon oil, citrus oil, rosemary oil, pyrethrum). The additional microorganism, pesticide, or agent may be applied prior to, at the same time, or after application of the *Daldinia* strain and/or VOCs produced therefrom.

Furthermore, the pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a Reynoutria extract.

The fungicide can also be a multi-site non-inorganic, chemical fungicide selected from the group consisting of chloronitrile, quinoxaline, sulphamide, phosphonate, phosphite, dithiocarbamate, chloralkylhios, phenylpyridinamine, and cyano-acetamide oxime.

As noted above, the composition may further comprise a nematicide. This nematicide may include but is not limited to chemicals such as organophosphates, carbamates, and fumigants, and microbial products such as avermectin, *Myrothecium* spp., Biome (*Bacillus firmus*), *Pasteuria* spp., *Paecilomyces* spp., and organic products such as saponins and plant oils.

In the case that the composition is applied to a seed, the composition may be applied to the seed as one or more coats prior to planting the seed using one or more seed coating agents including, but are not limited to, ethylene glycol, polyethylene glycol, chitosan, carboxymethyl chitosan, peat moss, resins and waxes or chemical fungicides or bactericides with either single site, multisite or unknown mode of action using methods known in the art.

The compositions set forth above can be formulated in any manner. Non-limiting formulation examples include but are not limited to Dried grains such as barley, corn, rye, rice, soy and wheat, Emulsifiable concentrates (EC), Wettable powders (WP), Soluble liquids (SL), Aerosols, Ultra-low volume concentrate solutions (ULV), Soluble powders (SP), Microencapsulation, Water dispersed granules (WDG), Flowables (FL), Microemulsions (ME), Nano-emulsions (NE), etc. In any formulation described herein, percent of the active ingredient is well within the skills of the artisan e.g., within a range of 0.01% to 99.99%.

The compositions may be in the form of a liquid, gel, solid, or biofumigant. A solid composition can be prepared by soaking a solid carrier in a solution of active ingredient(s) and drying the suspension under mild conditions, such as evaporation at room temperature or vacuum evaporation at 65° C. or lower. A solid composition can also be dried grains grown with the strain. The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B.

In another particular embodiment, the nonionic surfactant is polyoxyethylene (20) monolaurate. The concentration of surfactants may range between 0.1-35% of the total formulation, e.g., range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

As noted above, the compositions set forth above may be applied using methods known in the art. Specifically, these compositions may be applied to and around plants or plant parts. The plant or plant part may be pre-harvest (rooted in the soil or hydroponics, open field, greenhouse etc.) or post-harvest. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include, but are not limited to, harvested material, and vegetative and generative propagation material, for example cuttings, tubers, rhizomes, offshoots and seeds.

Plants that may be treated include but are not limited to: (A) Major edible food crops, which include but are not limited to (1) Cereals (e.g., African rice, barley, durum wheat, einkorn wheat, emmer wheat, finger millet, foxtail millet, hairy crabgrass, Indian barnyard millet, Japanese barnyard millet, maize, nance, oat, pearl millet, proso millet, rice, rye, sorghum, Sorghum spp., rye, spelt wheat); (2) Fruits (e.g., abiu, acerola, achacha, African mangosteen, alpine currant, ambarella, American gooseberry, American persimmon, apple, apricot, araza, Asian palmyra palm, Asian pear, atemoya, Australian desert raisin, avocado, azarole, babaco, bael, banana, Barbados gooseberry, bergamot, betel nut, bignay, bilberry, bilimbi, binjai, biriba, bitter orange, black chokeberry, black mulberry, black sapote, blackberry, blue-berried honeysuckle, borojo, breadfruit, murmese grape, button mangosteen, cacao, calamondin, canistel, cantaloupe, cape gooseberry, cashew nut, cassabanana, cempedak, charichuelo, cherimoya, cherry, cherry of the Rio Grande, cherry plum, Chinese hawthorn, Chinese white pear, chokeberry, citron, cocona, coconut, cocoplum, coffee, coffee Arabica, coffee robusta, Costa Rica pitahaya, currants, custard apple, date, date-plum, dog rose, dragonfruit, durian, elderberry, elephant apple, Ethiopian eggplant, European nettle tree, European wild apple, feijoa, fig, gac, genipapo, giant granadilla, gooseberry, goumi, grape, grapefruit, great morinda, greengage, guava, hardy kiwi, hog plum, horned melon, horse mango, Indian fig, Indian jujube, jabuticaba, jackberry, jackfruit, Japanese persimmon, Japanese wineberry, jocote, jujube, kaffir lime, karanda, kei apple, kepel apple, key lime, kitembilla, kiwi fruit, korlan, kubal vine, kuwini mango, kwai muk, langsat, large cranberry, lemon, Liberian coffee, longan, loquat, lychee, malay apple, mamey sapote, mammee apple, mango, mangosteen, maprang, marang, medlar, melon, Mirabelle plum, miracle fruit, monkey jack, moriche palm, mountain papaya, mountain soursop, mulberry, naranjilla, natal plum, northern highbush blueberry, olive, otaheite gooseberry, oval kumquat, papaya, para guava, passion fruit, pawpaw, peach, peachpalm, pear, pepino, pineapple, pitomba Eugenia luschnathiana, pitomba talisia esculenta, plantain, plum, pomegranate, pomelo, pulasan, purple chokeberry, quince, rambutan, ramontchi, raspberry, red chokeberry, red currant, red mulberry, red-fruited strawberry guava, rhubarb, rose apple, roselle, safou, salak, salmonberry, santol, sapodilla, satsuma, seagrape, soncoya, sour cherry, soursop, Spanish lime, Spanish tamarind, star apple, starfruit, strawberry, strawberry guava, strawberry tree, sugar apple, Surinam cherry, sweet briar, sweet granadilla, sweet lime, tamarillo, tamarind, tangerine, tomatillo, tucuma palm, *Vaccinium* spp., velvet apple, wampee, watermelon, watery rose apple, wax apple, white currant, white mulberry, white sapote, white star apple, wolfberry (*Lyceum barbarum, L. chinense*), yellow mombin, yellow pitaya, yellow-fruited strawberry, guava, (3) Vegetables (e.g., ackee, agate, air potato, *Amaranthus* spp., American groundnut, antroewa, armenian cucumber, arracacha, arrowleaf elephant ear, arrowroot, artichoke, ash gourd, asparagus, avocado, azuki bean, bambara groundnut, bamboo, banana, Barbados gooseberry, beet, beet root, bitter gourd, bitter vetch, bitterleaf, black mustard, black radish, black salsify, blanched celery, breadfruit, broad bean, broccoli, Brussels sprout, Buck's horn plantain, buttercup squash, butternut squash, cabbage, caigua, calabash, caraway seeds, carob, carrot, cassabanana, cassaya, catjang, cauliflower, celeriac, celery, celtuce, chard, chayote, chickpea, chicory, chilacayote, chili pepper (*Capsicum annuum, C. baccatum, C. chinense, C. frutescens, C. pubescens*), Chinese cabbage, Chinese water chestnut, Chinese yam, chives, chufa sedge, cole crops, common bean, common purslane, corn salad, cowpea, cress, cucumber, cushaw pumpkin, drumstick tree, eddoe, eggplant, elephant foot yam, elephant garlic, endive, enset, Ethiopian eggplant, Florence fennel, fluted gourd, gac, garden rocket, garlic, geocarpa groundnut, Good King Henry, grass pea, groundnut, guar bean, horse gram, horseradish, hyacinth bean, ice plant, Indian fig, Indian spinach, ivy gourd, Jerusalem artichoke, jacamar, jute, kale, kohlrabi, konjac, kurrat, leek, lentil, lettuce, Lima bean, lotus, luffa, maca, maize, mangelwurzel, mashua, moso bamboo, moth bean, mung bean, napa cabbage, neem, oca, okra, Oldham's bamboo, olive, onion, parsnip, pea, pigeon pea, plantain, pointed gourd, potato, pumpkins, squashes, quinoa, radish, rapeseed, red amaranth, rhubarb, ribbed gourd, rice bean, root parsley, runner bean, rutabaga, sago palm, salsify, scallion, sea kale, shallot, snake gourd, snow pea, sorrel, soybean, spilanthes, spinach, spinach beet, sweet potato, taro, tarwi, teasle gourd, tepary bean, tinda, tomato, tuberous pea, turnip, turnip-rooted chervil, urad bean, water caltrop *Trapa bicornis*, water caltrop *Trapa natans*, water morning slory, watercress, welsh onion, west African okra, west Indian gherkin, white goosefoot, white yam, winged bean, winter purslane, yacon, yam, yard-long bean, zucchini); (4) Food crops (e.g., abiu, acerola, achacha, ackee, African mangosteen, African rice, agate, air potato, alpine currant, *Amaranthus* spp., Ambarrella, American gooseberry, American groundnut, American persimmon, antroewa, apple, apricot, araza, Armenian cucumber, arracacha, arrowleaf elephant ear, arrowroot, artichoke, ash gourd, Asian palmyra palm, Asian pear, asparagus, atemoya, Australian desert raisin, avocado, azarole, azuki bean, babaco, bael, bambara groundnut, bamboo, banana, barbados gooseberry, barley, beet, beetroot, bergamot, betel nut, bignay, bilberry, bilimbi, binjai, biriba, bitter gourd, bitter orange, bitter vetch, bitterleaf, black chokeberry, black currant, black mulberry, black mustard, black radish, black salsify, black sapote, blackberry, blanched celery, blue-berried honeysuckle, borojo, breadfruit, broad bean, broccoli, Brussels sprout, Buck's horn plantain, buckwheat, Burmese grape, buttercup squash, butternut squash, button mangosteen, cabbage, cacao, caigua, calabash, calamondin, canistel, cantaloupe, cape gooseberry, caraway seeds, carob, carrot, cashew nut, cassaya, catjang, cauliflower, celeriac, celery, celtuce, cempedak, chard, charichuelo, chayote, cherimoya, cherry, cherry of the Rio Grande, cherry plum, chickpea, chicory, chilacayote, chili pepper (*Capsicum annuum, C. baccatum, C. chinense, C. frutescens, C. pubescens*), Chinese cabbage, Chinese hawthorn, Chinese water chestnut, Chinese white pear, Chinese yam, chives, chokeberry, chufa sedge, citron, cocona, coconut, cocoplum, coffee, coffee (Arabica and Robusta types), cole crops, common bean, common purslane, corn salad, Costa Rica pitahaya, cowpea, cress, cucumber, currants, cushaw pumpkin, custard apple, date, date-plum, dog rose, dragonfruit, drumstick tree, durian, durum wheat, eddoe, eggplant, einkorn wheat, elderberry, elephant apple, elephant foot yam, elephant garlic, emmer wheat, endive, enset, Ethiopian eggplant, European nettle tree, European wild apple, feijoa, fig, finger millet, Florence fennel, fluted gourd, foxtail millet, gac, garden rocket, garlic, genipapo, geocarpa groundnut, giant granadilla, good king henry, gooseberry, goumi, grape, grapefruit, grass pea, great morinda, greengage, groundnut, grumichama, guar bean, guava, hairy crabgrass, hardy kiwi, hog plum, horned melon, horse gram, horse mango, horseradish, hyacinth bean, iceplant, Indian barnyard millet, Indian fig, Indian jujube, Indian spinach, ivy gourd, jabuticaba, jackalberry, jackfruit, jambul, Japanese barnyard millet, Japanese persimmon, Japanese wineberry, Jerusalem artichoke, jocote, jujube, jute, kaffir lime, kale, karanda, kei apple, kepel apple, key lime, kitembilla, kiwifruit, kohlrabi, konjac, korlan, kubal vine, kurrat, kuwini mango, kwai muk, langsat, large cranberry, leek, lemon, lentil, lettuce, Liberian coffee, lima bean, longan, loquat, lotus, luffa, lychee, maca, maize, malay apple, mamey saptoe, mammee apple, mangel-wurzel, mango, mangosteen, maprang, marang, mashua, medlar, melon, Mirabelle plum, miracle fruit, monk fruit, monkey jack, moriche palm, moso bamboo, moth bean, mountain papaya, mountain soursop, mulberry, mung bean, mushrooms, nance, napa cabbage, naranjilla, natal plum, neem, northern highbush blueberry, oat, oca, oil palm, okra, old man's bamboo, olive, onion, orange, otaheite gooseberry, oval kumquat, papaya, para guava, parsnip, passionfruit, pawpaw, pea, peach, peach-palm, pear, pearl millet, pepino, pigeon pea, pineapple, Pitomba (Eugenia luschnathiana, Talisia esculenta), plantain, plum, pointed gourd, pomegranate, pomelo, potato, proso millet, pulasan, pumpkins and squashes, purple chokeberry, quince, quinoa, radish, rambutan, ramontchi, rapeseed, raspberry, red amaranth, red chokeberry, red currant, red mulberry, red-fruited strawberry guava, rhubarb, ribbed gourd, rice, rice bean, root parsley, rose apple, roselle, runner bean, rutabaga, rye, safou, sago palm, salak, salmonberry, salsify, santol, sapodilla, Satsuma, scallion, sea kale, seagrape, shallot, snake gourd, snow pea, soncoya, sorghum, *Sorghum* spp., sorrel, sour cherry, soursop, soybean, Spanish lime, Spanish tamarind, spelt wheat, spilanthes, spinach, spinach beet, star apple, starfruit, strawberry, strawberry guava, strawberry tree, sugar apple, sugar beet, sugarcane, surinam cherry, sweet briar, sweet granadilla, sweet lime, sweet potato, tamarillo, tamarind, tangerine, taro, tarwi, teasle gourd, tef, tepary bean, tinda, tomatillo, tomato, tuberous pea, tucuma palm, turnip, turnip-rooted chervil, urad bean, *Vaccinium* spp., velvet apple, wampee, water caltrop (*Trapa bicornis, T. natans*), water morning glory, watercress, watermelon, watery rose apple, wax apple, welsh onion, west African okra, west Indian gherkin, wheat, white currant, white goosefoot, white mulberry, white sapote, white star apple, white yam, winged bean, winter purslane, wolfberry (*Lycium barbarum, L. chinense*), yacon, yam, yangmei, yard-long bean, yellow mombin, yellow pitaya, yellow-fruited strawberry guava, zucchini; (B) Other edible crops, which includes but is not limited to (1) Herbs (e.g., *Absinthium*, alexanders, basil, bay laurel, betel nut, camomile, chervil, chili pepper (*Capsicum annuum, C. baccatum, C. chinense, C. frutescens, C. pubescens*), chili peppers, chives, cicely, common rue, common thyme, coriander, cress, culantro, curly leaf parsley, dill, epazote, fennel, flat leaf parsley, ginseng, gray santolina, herb hyssop, holy basil, hop, jasmine, kaffir lime, lavender, lemon balm, lemon basil, lemon grass, lovage, marjoram, mint, oregano, parsley, peppermint, perilla, pot marigold, rooibos, rosemary, sage, shiny-leaft buckthorn, sorrel, spearmint, summer savory, tarragon, That basil, valerian, watercress, wild betel, winter savory, yerba mate); (2) Spices (e.g., ajowan, allspice, anise, bay laurel, black cardamom, black mustard, black pepper, caper, caraway seeds, cardamom, chili pepper (*Capsicum annuum, C. baccatum, C. chinense, C. frutescens, C. pubescens*), chili peppers, cinnamon, clove, common juniper, coriander, cumin, fennel, fenugreek, garlic, ginger, kaffir lime, liquorice, nutmeg, oregano, pandan, parsley, saffron, star anise, turmeric, vanilla, white mustard); (2) Medicinal plants (e.g., absinthium, alfalfa, aloe vera, anise, artichoke, basil, bay laurel, betel leaf, betel nut, bilberry, black cardamom, black mustard, black pepper, blue gum, borojo, chamomile, caper, cardamom, castor bean, chili peppers, Chinese yam, chives, cola nut, common jasmine, common lavender, common myrrh, common rue, cilantro, cumin, dill, dog rose, epazote, fennel, fenugreek, gac, garlic, ginger, gray santolina, gum Arabic, herb hyssop, holy basil, horseradish, incense tree, lavender, lemon grass, liquorice, lovage, marijuana, marjoram, monk fruit, neem, opium, oregano, peppermint, pot marigold, quinine, red acacia, red currant, rooibos, safflower, sage, shiny-leaf buckthorn, sorrel, spilanthes, star anise, tarragon, tea, turmeric, valerian, velvet bean, watercress, white mustard, white sapote, wild betel, wolfberry (*Lycium barbarum, L. chinense*), yerba mate); (3) Stimulants (e.g., betel leaf, betel nut, cacao, chili pepper (*Capsicum annuum, C. baccatum, C. chinense, C. frutescens, C. pubescens*), chili peppers, coffee, coffee (*Arabica, Robusta*), cola nut, khat, Liberian coffee, tea, tobacco, wild betel, yerba mate); (4) Nuts (e.g., almond, betel nut, Brazil nut, cashew nut, chestnut, Chinese water chestnut, coconut, cola nut, common walnut, groundnut, hazelnut, Japanese stone oak, macadamia, nutmeg, paradise nut, pecan nut, pistachio nut, walnut); (5) Edible seeds (e.g., black pepper, Brazil nut, chilacayote, cola nut, fluted gourd, lotus, opium, quinoa, sesame, sunflower, water caltrop (*Trapa bicornis, T. natans*)); (6) Vegetable oils (e.g., black mustard, camelina, castor bean, coconut, cotton, linseed, maize, neem, Niger seed, oil palm, olive, opium, rapeseed, safflower, sesame, soybean, sunflower, tung tree, turnip); (7) Sugar crops (e.g., Asian palmyra palm, silver date palm, sorghum, sugar beet, sugarcane); (8) Pseudocereals (e.g., *Amaranthus* spp., buckwheat, quinoa, red amaranth); (9) Aphrodisiacs (e.g., borojo, celery, durian, garden rocket, ginseng, maca, red acacia, velvet bean); (C) Non food categories, including but not limited to (1) forage and dodder crops (e.g., agate, alfalfa, beet, broad bean, camelina, catjang, grass pea, guar bean, horse gram, Indian barnyard millet, Japanese barnyard millet, lespedeza, lupine, maize, mangel-wurzel, mulberry, Niger seed, rapeseed, rice bean, rye); (2) Fiber crops (e.g., coconut, cotton, fique, hemp, henequen, jute, kapok, kenaf, linseed, manila hemp, New Zealand flax, ramie, roselle, sisal, white mulberry); (3) Energy crops (e.g., blue gum, camelina, cassaya, maize, rapeseed, sorghum, soybean, Sudan grass, sugar beet, sugarcane, wheat); (4) Alcohol production (e.g., barley, plum, potato, sugarcane, wheat, sorghum); (5) Dye crops (e.g., chay root, henna, indigo, old fustic, safflower, saffron, turmeric); (6) Essential oils (e.g., allspice, bergamot, bitter orange, blue gum, camomile, citronella, clove, common jasmine, common juniper, common lavender, common myrrh, field mint, freesia, gray santolina, herb hyssop, holy basil, incense tree, jasmine, lavender, lemon, marigold, mint, orange, peppermint, pot marigold, spearmint, ylang-ylang tree); (6) Green manures (e.g., alfalfa, clover, lacy Phacelia, sunn hemp, trefoil, velvet bean, vetch); (7) Erosion prevention (e.g., bamboo, cocoplum); (8) Soil improvement (e.g., lupine, vetch); (9) Cover crops (e.g., Alfalfa, lacy Phacelia, radish); (10) Botanical pesticides (e.g., jicama, marigold, neem, pyrethrum); (11) Cut flowers (e.g., carnation, chrysanthemum, daffodil, dahlia, freesia, gerbera, marigold, rose, sunflower, tulip); (12) Ornamental plants (e.g., African mangosteen, aloe vera, alpine currant, aster, black chokeberry, breadfruit, calamondin, carnation, cassabanana, castor bean, cherry plum, chokeberry, chrysanthemum, cocoplum, common lavender, crocus, daffodil, dahlia, freesia, gerbera, hyacinth, Japanese stone oak, Jasmine, lacy Phacelia, lotus, lupine, marigold, New Zealand flax, opium, purple chokeberry, ramie, red chokeberry, rose, sunflower, tulip, white mulberry); (D) Trees which include but are not limited to abelia, almond. apple, apricot, arborvitae nigra American, arborvitae, ash, aspen, azalea, bald cypress, beautybush, beech, birch, black tupelo, blackberry, blueberry, boxwood, buckeye, butterfly bush, butternut, camellia, catalpa, cedar, cherry, chestnut, coffee tree, crab trees, crabapple, crape myrtle, cypress, dogwood, Douglas fir, ebony, elder American, elm, fir, forsythia, ginkgo, goldenraintree, hackberry, hawthorn, hazelnut, hemlock, hickory, holly, honey locust, horse chestnut, hydrangea, juniper, lilac, linden, magnolia, maple, mock orange, mountain ash, oak, olive, peach, pear, pecan, pine, pistachio, plane tree, plum, poplar, pivet, raspberry, redbud, red cedar, redwood, rhododendron, rose-of- Sharon, sassafras, sequoia, serviceberry, smoke tree, soapberry, sourwood, spruce, strawberry tree, sweet shrub, sycamore, tulip tree, ciborium, walnut, weasel, willow, winterberry, witch-hazel, zelkova; (E) Turf, which includes but is not limited to Kentucky bluegrass, tall fescue, Bermuda grass, zoysia grass, perennial ryegrass, fine fescues (e.g. creeping red, chewings, hard, or sheep fescue).

As mentioned the plant, part thereof or the phytopathogens are exposed to an effective amount of the composition. Exposure as used herein means that a sufficient amount of the VOC(s) effect the killing of the phytopathogen or reduce growth thereof.

Exposing the plant, part thereof or the phytopathogen to the compositions set forth above may be carried out directly or by allowing the compositions to act on their surroundings, habitat or storage space by, for example, immersion, coating, dipping, spraying, evaporation, fogging, scattering, painting on, injecting.

The compositions may also be applied to the soil using methods known in the art. These include but are not limited to (a) drip irrigation or chemigation; (b) soil incorporation; (c) seed treatment.

The compositions, be used as pesticides and in particular, may be used as insecticides, nematicides, fungicides and bactericides, alone or in combination with one or more pesticidal substances set forth above and applied to plants, plant parts, substrate for growing plants or seeds.

The compositions may be combined with other enhancing compounds for the compositions such as, but not limited to, amino acids, chitosan, chitin, starch, hormones, minerals, synergistic microbes to increase efficacy and promote benefits to plants.

The phytopathogenic activity of the compositions of the invention as well as their sprouting inhibition activity renders these compositions, an optimal treatment for enhancing storage of harvested plants or plant parts.

Thus, according to an additional aspect there is provided a method of storing a plant or plant part, the method comprising exposing a post harvest plant or plant part to an effective amount of a composition comprising a biologically pure culture of *Daldinia* sp. or at least one volatile organic compound (VOC) being produced by the biologically pure culture and capable of killing a phytopathogen or reducing growth thereof, thereby storing the plant or plant part.

Thus, the fungi and the gases produced by the fungi are useful to inhibit the growth of or kill a phytopathogen selected from the group consisting of a fungus, a bacteria, a microorganism, a nematode and an insect. The fungi or VOCs described herein can be used to improve storage of harvested plant materials. Alternatively, the fungi and/or VOC(s) can be used to treat human or animal waste, e.g., as a component of a waste water or solid management or treatment. They also are useful to decontaminate human and animal waste, e.g., decrease or remove bacterial and fungal contamination. Yet further, the fungi and/or its VOC(s) can be used to treat or prevent toxic mold on building materials and in buildings by contacting the building, the building materials, or the spaces between the building materials with an effective amount of the volatile byproduct.

According to another embodiment of the present invention, the biologically active bio-control agent comprising emitted VOCs can be employed as an attractant of insects or pests, e.g., in traps, to detect or control infestations of insects or pests, thereby preventing or diminishing the pest reproduction in closed places such as greenhouses.

According to some embodiments of the present invention, the biologically active bio-control agent comprising emitted VOCs can be used in pharmaceutical and cosmetic preparations containing other active compounds having antibiotic or antimicrobial activities and additives selected from carriers, colorants, dispersing agents, emulsifying agents, fillers, gelling agents, humectants, preservatives, solubilizing agents, surfactants, thickening agents and combinations thereof.

It is expected that during the life of a patent maturing from this application many relevant carriers will be developed and the scope of the term carrier is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Fungal Isolation, Maintenance and Growth Conditions

The culture of *D. concentrica* isolate, used in this study, was obtained as an endophyte from a small limb of an olive tree (*Olea europaea* L.) located in the Ha'Ela Valley at the Judea foothills in Israel. Wood pieces were surface sterilized by submersion in ethanol for 10 seconds followed by flaming. Small pieces were cut and placed on potato dextrose agar (PDA, Acumedia, USA) amended with tetracycline at 12 µg/mL (Sigma, Israel), and incubated at 25° C. After 5 days, isolated fungal hyphal tips that emerged from the plant material to the PDA, were removed with a syringe needle and transferred to a new PDA-tetracycline plate. A single spore colony was used throughout this study. The culture was maintained routinely on PDA-tetracycline plates and incubated at 25° C. Fresh fungal mycelium was transferred every 2 weeks to a new plate. The fungus was stored by either freezing small agar plagues in 30% glycerol in −80° C. or by growing the fungus on autoclaved sweet corn seeds at 25° C.

The *D. concentrica* isolate was grown on different natural and synthetic media. All natural media: corn flour, crushed wheat, lentils, rice, corn, chickpea, and oat, were bought in commercial stores, soaked with water and autoclaved. The synthetic media: PDA, potato dextrose broth (PDB), nutrient agar (NA), Luria-Bertani (LB) agar, and tryptic soy agar were purchased from Acumedia, whereas lima bean agar was purchased from Difco (Michigan, USA), and agar-agar for the agar-water medium was purchased from Romical (Be'er Sheva, Israel). All synthetic media were prepared according to manufacturer instructions.

Test fungi: *Pythium ultimum, Pythium aphanidermatum, Alternaria alternata* pathotype tangelo, *Fusarium oxysporum, Fusarium euwallaceae, Fusarium mangiferae, Coniella* sp., *Phoma tracheiphila, Colletotrichum* sp., *Rhizoctonia solani, Alternaria alternata, Botrytis cinerea, Sclerotinia sclerotiorum, Penicillium digitatum, Lasiodiplodia theobromae, Neoscytalidium dimidiatum* and *Aspergillus niger*, were grown on PDA amended with tetracycline at 12 µg/mL, and incubated at 25° C., except *Pythium* sp. that were grown on PDA without tetracycline.

Isolation of Fungal DNA

Squares (0.5 cm$^2$) from 7-day-old, single-spore mycelial cultures grown on PDA at 25° C., were cut with a sterile scalpel and the agar was scraped from the bottom of each piece to exclude as much agar as possible. The pieces were homogenized in liquid nitrogen using a mortar and pestle. DNA was then extracted using the GenElute Plant Genomic DNA Miniprep Kit (Sigma) according to the manufacturer's instructions. Amplification of internal transcribed spacer-5.8S rDNA and partial actin gene are further described hereinbelow.

*D. concentrica* Bioactivity Tests

The activity of *D. concentrica* volatiles was examined using the "Sandwich Method". In this method no direct contact between *D. concentrica* and the test fungi is possible. Thus, the effect of the former on the growth of the latter is only due to the volatiles produced by *D. concentrica* that spread freely across the plates. A plug of PDA harboring the *D. concentrica* mycelia was added to 50 mm Petri dish containing 5 mL PDB, or any other growth medium to be examined, and let to grow at 25° C. for 3-4 days. Then, a plug of PDA harboring mycelia of the test fungus was added to another 50 mm Petri dish containing PDA, and the PDA Petri dish with the test fungus was put on top of the *D. concentrica* containing Petri dish. Both Petri dishes were connected without their covers using parafilm and let to grow at 25° C. The effect of *D. concentrica* on the test fungi was examined after 2 days, and compared to the growth of the same test fungi in the absence of *D. concentrica*. All experiments were performed in triplicates.

The inhibitory effect of *D. concentrica* on various plant pathogenic fungi was examined as described above except that *D. concentrica* was grown for 6 days prior the addition of the test fungi, and the inhibition was examined after 6 days of incubation. At the end of the assay, the viability of each test fungi was evaluated by transferring inoculum plugs to fresh PDA plates and observing the growth that developed within the next two days.

The temperature range that supported *D. concentrica* growth and activity was examined as follows: *D. concentrica* was grown in 50 mm Petri dish containing 5 mL PDB at various temperatures: 10, 15, 18, 20, 22, and 25° C. and the growth were monitored for 6 days. For activity tests at 15 and 18° C., *D. concentrica* was grown in 50 mm Petri dish containing 5 mL PDB for 7 days at these temperatures before the addition of *A. niger* as the test fungus. Both fungi were connected in the "Sandwich Method" as described above, and the growth of the test fungus was monitored after 4 days, and compared to the growth of *A. niger* grown under the same conditions in the absence of *D. concentrica*. The activity test at 10° C. was performed similarly, except that the test fungi were *A. alternata*, *B. cinerea*, and *P. digitatum* instead of *A. niger* since the latter did not grow at 10° C. even in the absence of the volatiles, and that *D. concentrica* was grown for ~1 month before introducing the test fungi, and those fungi were exposed for *D. concentrica* volatiles for 13 days.

Organic dried plum, raisin and apricot were bought commercially. The experiment (triplicates, 2 biological repetitions) was performed in sealed 1 L boxes. Each box contained zero, one or two 50 mm Petri dish containing 5 mL PDB and a plug of *D. concentrica*. The fungi let to grow in the sealed boxes for 3-4 days at 25° C. Then, 120 g from each dried fruit was incubated at room temperature with excess of sterile double distilled water for 3-4 hours. Next, the swelled dried fruit were put in 50 mm Petri dish (each type to a different plate) and placed in the *D. concentrica* containing boxes, or the control boxes without the fungus. The boxes were further incubated at 25° C. for 6-9 days before estimating fungal appearance from the swelled dried fruit.

Peanuts were bought commercially and prearranged in 50 mm Petri dish (4 peanuts per plate, triplicates, and 2 biological repetitions) in the presence of 5 mL sterile double distilled water. Then, all peanuts were inoculated with drops (10 µL, 3 drops for each peanut) of *A. niger* conidial suspension ($10^6$ conidia/mL). Next, each peanuts Petri dish was transferred to a sealed 1 L box that contained zero, one or two 50 mm Petri dish containing *D. concentrica* that was pre-grown for 3-5 days at 25° C. The boxes were further incubated for 10 days at 25° C. before estimating *A. niger* development on peanuts.

Volatiles Identification

*D. concentrica* was grown on PDB (5 mL) in sealed solid-phase microextraction (SPME) 20 mL vials. A Plug of growing mycelium was placed in each vial and incubated at 25° C. for three days. The vial was preheated to 40° C. for 15 min, then an automatic HS-SPME MPS2 (Gerstel, Mülheim, Germany) with 65 m PDMS/DVB/CAR fiber (polydimethyl siloxane/divinylbenzene/carboxen) (Supelco, PA, USA) was inserted into the samples headspace for 25 min. The exposed SPME syringe was introduced into the injector port of a GC-MS apparatus for 10 min. Volatile compounds were analyzed on a GC-MSD apparatus (6890/5973N Agilent Technologies CA, USA) equipped with an Rxi-5 SIL MS (30 m*0.25 mm*0.25 m) fused-silica capillary Column (Restek). Helium (Constant pressure 9.1 psi) was used as a carrier gas. The injector temperature was 250° C., set for splitless injection. The oven was set to 50° C. for 1 min, and then the temperature was increased to 180° C. at a rate of 5° C./min, then to 280° C. at 25° C./min. The detector temperature was 280° C. The mass range was recorded from 41 to 350 m/z, with electron energy of 70 eV. A mixture of straight-chain alkanes (C7-C23) was injected into the column under the above-mentioned conditions for determination of retention indices. The GC-MS spectrum profiles were analyzed using the ChemStation software. Identification of the volatiles was assigned by comparison of their retention indices with those of literature and by comparison of spectral data with standard or with the W9N08 and HPCH2205 GC-MS libraries, and NIST Mass Spectral Library, ver. 2.0d. Comparable analyses were conducted on SPME vials containing only PDB, and the compounds obtained therefrom were subtracted from the analysis done on vials containing the fungus.

For quantitative analysis, samples were prepared by mixing 13 g sample and 5 g NaCl with chlorobenzene before injection to the GC-MS. All samples were prepared in duplicates. For the chemical compounds: 3-methyl-1-butanol, (±)-2-methyl-1-butanol, 4-heptanone, isoamyl acetate, and trans-2-octenal, confirmatory identification was made by comparing the GC-MS data of available authentic standards, obtained from Sigma, with the GC-MS data of fungal products.

Chemical Mixtures Bioactivity Tests

All chemical compounds were purchased from Sigma (Rehovot, Israel) and were of the highest purity available. The bioactivity of the mixtures combined on the VOCs identified, was determined as follows: Petri dishes (90 mm, 80 mL air volume) containing 15 mL of media (PDA amended with 12 µg/mL tetracycline) were inoculated (triplicates, 2 plugs each) with the test fungi *A. alternata* and *B. cinerea* (in the same plate), *P. digitatum* and *A. niger* (in separate plates). A cup of an Eppendorf tube was placed in the middle of the plate to which increasing volumes (0-200 µL) of the mixture was added. Then, the plates were sealed with parafilm and incubated at room temperature for two days before comparing the growth of the test fungi in those plates to control plates in the absence of the mixture. The ability of two mixtures: Mixture A and Mixture B to control other plant pathogenic fungi was determined as described above except that the concentration of the mixture was constant (1 mL/L) and the growth inhibition was estimated after 6 days. The viability of the test fungi after exposure to the mixtures was examined as described for *D. concentrica*.

The activity of each chemical component of the mixture was examined separately as described for the mixtures. For "Mixture A" the volumes were 16, 16, 32, and 16 µL for 3-methyl-1-butanol, (±)-2-methyl-1-butanol, 4-heptanone, and isoamyl acetate, respectively. For "Mixture B" the volumes were 40 µL each for 4-heptanone and trans-2-octenal.

The ability of the mixtures to inhibit the growth of *A. alternata, B. cinerea, P. digitatum*, and *A. niger* was examined in temperature range of 4, 10, 15, 18, 20, 22, and 25° C. The experiment was performed in sealed 1 L boxes (3 boxes per temperature). Each box contained 4 PDA Petri dishes (one for each test fungus) without their covers and the mixture was located on the opposite side of the box. "Mixture A" (1 mL/L) was deposited in a vial (12×35 mm, Fisher Scientific), whereas "Mixture B" (0.05 mL/L) was placed on laboratory absorbent paper (8×3 cm). For each temperature, a control box, containing triplicates of the four test fungi in the absence of mixture, was prepared. The boxes were incubated for two weeks before evaluation of fungal growth.

Wheat grains were bought commercially and prearranged in 50 mm Petri dish (8 g wheat grains per plate, triplicates, and 2 biological repetitions). Each sealed 1 L box contained one Petri dish with wheat grains, one Petri dish with 5 mL distilled water, and a piece of a laboratory absorbent paper (8×3 cm) adsorbed with 0, 0.25, 0.5, or 1 mL/L of either "Mixture A" or "Mixture B". The boxes were incubated for 10 days at 25° C. before visual evaluation of fungal appearance from the wheat grains.

The effect of the mixtures on *A. niger* development on peanuts was examined as follows: peanuts (4 peanuts per plate, triplicates, and 2 biological repetitions) in the presence of 5 mL sterile double distilled water were incubated in sealed 1 L boxes in the presence of a vial (12×35 mm) containing 1 mL/L of "mixture A" at room temperature. Half of the peanuts were pre-inoculated with *A. niger* conidial suspension ($10^6$ conidia/mL) as described above. Inoculated or non-inoculated control peanuts were incubated under the same conditions in the absence of the mixture. Intrinsic and artificial development of *A. niger* was evaluated after 10 days. "Mixture B" was similarly examined except that the incubation time was 8 days, and that instead of vials the mixture was deposited on a piece of a laboratory absorbent paper (8×3 cm) at concentrations of 0, 0.05, 0.25, and 0.5 mL/L, and that the peanuts were not artificially inoculated with *A. niger*, but rather the fungal development was from an intrinsic source. The effect of individual chemical compounds on peanuts germination and development of *A. niger* was examined as follows: peanuts (4 peanuts in each 50 mm Petri dish in the presence of 5 mL distilled water) were placed in sealed 1 L boxes (2 Petri dishes per box). Increasing concentrations (0, 0.25, 0.5, 0.75, 1.0, 1.25 mL/L) of the chemical compound (3-methyl-1-butanol, (±)-2-methyl-1-butanol, 4-heptanone, and isoamyl acetate) were deposited each in separate vials (12×35 mm). Half of the peanuts (4 peanuts in one Petri dish per box) were artificially inoculated with *A. niger* as described above. The boxes were incubated at room temperature for a week before estimation of peanuts germination and *A. niger* establishment. The effect of trans-2-octenal on peanuts germination was examined similarly except that the concentration of the chemical compound was 1 mL/L, the peanuts were not inoculated with *A. niger*, and the incubation time was 4 days.

Nematode Preparation

*Meloidogyne javanica* was propagated on greenhouse-grown nematode susceptible tomato *Lycopersicon esculentum* cv. "Avigail 870" (Hazera, Shikmim, Israel) and nematodes eggs were bulk extracted from the roots with 0.05% (v/v) sodium hypochlorite (NaOCl) following by sucrose floatation and passing through sieves of 300, 60, and 30 µm (nylon net, AD Sinun Technologies, Petach Tikvah, Israel), allowing collection of pure eggs solution in the lower sieve. For second stage juveniles hatching, extracted eggs were placed on 30 m (AD Sinun Technologies) opening sieves in 0.01 M MES (2-(N-Morpholino)ethanesulfonic acid hydrate) (Sigma) buffer under aseptic dark conditions for 3 days and hatching J2 were collected for further experiments. For soil inoculation tests, heavily infected susceptible tomato roots cv. "Avigail 870" (Hazera) were processed in a Waring (Waring, Torrington, CT) commercial blender for 2 min at high speed. A small portion of blended roots was taken to evaluate eggs concentration using 0.05% (v/v) sodium hypochlorite (NaOCl) extraction, as described above. The blended roots were used for soil inoculation in following experiments.

In Vitro Experiments Setup Using *D. concentrica* Culture

For In vitro studies of the bionematicidal activity of *D. concentrica* toward *M. javanica* J2s, pure culture plates of the fungus were prepared as follow: a plug of *D. concentrica* was transferred to a 50 mm Petri plate containing 5 mL potato dextrose broth (PDB, Acumedia, USA), and let to grow for 4-5 days for the subsequent experiments. *M. javanica* eggs or second stage juveniles (J2s) were obtained as described above. In vitro tests (duplicates for each treatment, 3 independent experiments) were performed in sealed 1 L boxes in which 1-3 culture plates of *D. concentrica* without their covers were placed. Five small vials (12×35 mm, Fisher Scientific) each containing 300 *M. javanica* J2 larvae in 0.5 mL of 0.01M MES were also subjected to each sealed box. In order to maintain humid environment, each sealed box was equipped with 5 mL sterile double distilled $H_2O$. A 5 mL PDA plate cultured with a fresh plug of *Aspergillus niger*, was added into each sealed box. Inhibition of *A. niger* by *D. concentrica* was reported previously, and was used as a positive internal control in our system while no effect of *A. niger* on J2s viability was found (data not shown). Sealed boxes carrying the described biological agents were incubated for 2 days before counting J2 viable larvae. All incubations were performed in the dark at 25±1° C.

In Vitro Experiments Using Synthetic Composed Mixture

All compounds were purchased from Sigma (Israel) with the highest purity available. The synthetic mixture contained the following compounds: 3-methyl-1-butanol, (±)-2-methyl-1-butanol, 4-heptanone, and isoamyl acetate in the ratio of 1:1:2:1. Each sealed 1 L box was arranged as described above, except that instead of *D. concentrica* culture plates, the synthetic mixture (1 mL/L) was loaded into one single vial (12×35 mm, Fisher Scientific), while no *A. niger* culture plate was used. The boxes (duplicates for each treatment, 3 independent experiments) were sealed and incubated as described above before counting. Determination of the individual nematicidal activity of each chemical compound was carried out as described for the synthetic mixture, except that each box (duplicates, 3 independent experiments) contained one vial loaded with the relative amount of the chemical used in the synthetic mixture: 161.8, 163.8, 326.8, and 175.2 mg for 3-methyl-1-butanol, (±)-2-methyl-1-butanol, 4-heptanone, and isoamyl acetate, respectively. For determination of the nematicidal activity of 4-heptanone, the following treatments were used (326.8 mg of 4-heptanone, duplicates, 3 independent experiments): a) incubation of nematodes for 24 hours in the presence of 4-heptanone, b) incubation of nematodes for 24 hours in the absence of the compound, c) incubation of nematodes for 24 hours in the presence of 4-heptanone and then the nematodes were transferred to recover in new boxes in the absence of the compound for additional 24 hours, d) incubation of nematodes for 48 hours in the presence of 4-heptanone, e) incubation of nematodes for 48 hours in the absence of the compound. The boxes were prepared with the nematodes and water as described above. All incubations were performed in the dark at 25±1° C.

For studying the effects of the fungus and the synthetic mixture on *M. javanica* eggs hatching, eggs suspension of *M. javanica*, extracted using the NaOCl method as described above, was determined for eggs concentration. For experiment setup, sealed 1 L boxes were arranged as follows: control boxes that contained 5 mL sterile double distilled $H_2O$ as a source of humidity, five small vials (12×35 mm, Fisher Scientific) each containing 800 *M. javanica* eggs in 0.5 mL of 0.01M MES, and one uncovered 50 mm Petri plate with 5 mL PDA and a fresh plug of *A. niger*. The *D. concentrica* and synthetic mixture containing boxes were prepared as described for the control except that 3 culture plates of *D. concentrica*, pregrown for 5 days, were added without their covers for the former, and one 50 mm Petri plate containing 125 mg perlite particles loaded with 250 L of the synthetic mixture was prepared for the latter. The boxes (duplicates for each treatment, 3 independent experiments) were incubated for 2 days. Then, the *M. javanica* eggs were collected from the vials, loaded on 30 m filters (AD Sinun Technologies), and inserted into 15 mL falcon tubes containing 0.01M MES buffer (900 μL) in order to discard all the larvae that hatched before the completion of the exposure to the volatiles. After 3 hours of incubation, the filters were removed to new 15 mL falcon tubes containing fresh MES buffer as above, and incubated for additional 2 days for hatching. The viable larvae, which hatched from eggs that were exposed for 2 days to the volatiles, were counted using hemocytometer as described below. All incubations were performed in the dark at 25±1° C.

Nematodes viability—to evaluate second stage juveniles viability at the end of incubation time, all nematodes were loaded on 30 m filter (AD Sinun Technologies) allowing active passing of living larvae through. The larvae (J2) were incubated on the filter for 3 hours in the dark at 25±1° C., and the viable nematodes, which were able to actively cross the filter, were counted using Nematode Precision Chambered (Chalex LLC, Portland, USA) and inverted microscope (Wilovert Standard, Helmut Hund GmbH, Wetzlar, Germany).

Soil Experimental Setup

Perlite particles were loaded with increasing concentrations of the synthetic mixture (0, 0.08, 0.17, 0.25, 0.33, 0.5 μL/g soil) at ratio of 1:1 between the perlite particles and the mixture. Then, the loaded particles were poured into 50 mL plastic cups pre-filled with 60 g of 10% humid loam soil (Givat Ada, Israel). The cups (5 cups per concentration, 2 independent experiments) were shook thoroughly before the addition of *M. javanica* J2 larvae (500 in 0.5 mL of 0.01M MES) to a small pit at the top of the soil. The cups were sealed and incubated for 2 days in the dark at 25±1° C. Viable J2 nematodes were determined by using the Bearmann apparatus.

Greenhouse Experimental Setup

Perlite particles (400 mg per pot) were loaded with either 0 or 400 μL (10 pots for each concentration) of the synthetic mixture before addition of 10% humid loam soil (800 g) containing a slow release fertilizer (Osmocote®, Scotts® Australia) and shaking till homogenization. Then, 10 pots (5 with mixture and 5 without mixture) were juvenile inoculated by the addition of 4000 *M. javanica* J2 larvae (in 5 mL of 0.01M MES), whereas the other 10 pots (5 with mixture and 5 without mixture) were inoculated using a 5 mL suspension of nematode inoculated roots (equivalent to ~4000 *M. javanica* eggs). All pots were sealed and incubated for 3 days in the dark at 25±2° C. Next, covers were removed and susceptible tomato seedling (4 weeks old) "Avigail 870" (Hazera) were planted. The seedlings were grown for 7 weeks at 25±2° C. (16/8 h day/night) with irrigation of 20 mL water per day, before symptoms evaluation. A second repetition of the greenhouse experiment was done as above, except that the soil was inoculated with the nematodes (either J2 larvae or suspension of nematode inoculated roots) 3 days before the addition of the synthetic mixture. Then, the nematode inoculated soil and volatile mixture were mixed, sealed and incubated for additional 3 days in the dark at 25±2° C. before tomato planting. The seedlings were grown for 8 weeks as above.

At the end of the experiments, plants along with their root systems were harvested from their pots. For evaluating disease development on roots, soil debris was removed carefully from washed root systems and root galling incidences were visually evaluated along with root weight measurements. For evaluating nematode reproduction on root systems, *M. javanica* eggs were extracted from each root and counted. The ratio of eggs per gram root was calculated.

Example 1

This example demonstrates the isolation of *D. concentrica*.

*D. concentrica* was obtained as an endophyte from a limb of an olive tree (*Olea europaea* L.). Pieces of wood were surface-sterilized by submersion in ethanol for 10 seconds, followed by flaming. Small pieces were cut and placed onto plates of PDA (Acomedia, Lansing, MI, USA). The plates were incubated at 25° C. Five days later, fungal hyphae had emerged from the plant material on the PDA. Isolated hyphal tips were removed with a syringe needle and transferred to new PDA plates. A single spore colony was used throughout this study. A, strong, sweet and fruity odor was detected when the culture plates of the *D. concentrica* isolate were opened.

Example 2

This example demonstrates the molecular identification of fungal DNA of *D. concentrica*.

Squares (0.5 cm$^2$) from a 14 days old, pure, single spore fungal culture mycelia, growing on PDA at 25° C., were cut with a sterile scalpel and the agar was scraped from the bottom of each piece, in order to exclude as much agar as possible. The pieces were ground in the presence of liquid nitrogen using mortar and pestle. The DNA was then extracted according to the manufacturer's instructions using the GenElute™ Plant Genomic DNA Miniprep Kit (Sigma, Rehovot, Israel). Extracted DNA samples were used for PCR amplification. Amplification of internal transcribed spacer sequences (ITS) 5.8S rDNA and actin gene was carried out as follows: The ITS regions were amplified using PCR with primers ITS1 (5' TCCGTAGGT-GAACCTGCGGG 3', SEQ ID NO: 3) and ITS4 (5' TCCTCCGCTTATTGATATGC 3', SEQ ID NO: 4). Part of the actin gene was amplified using PCR with primers ACT512F (5' ATGTGCAAGGCCGGTTTCGC 3', SEQ ID NO: 5) and ACT783R (5' TACGAGTCCTTCTGGCC-CAT 3', SEQ ID NO: 6). The PCR procedure was carried out in a 25 μL reaction mixture containing 10 ng DNA extracted from the fungal culture, 1 μL (10 μM) primer ITS1/ACT512F and 1 μL (10 μM) primer ITS4/ACT783R (Sigma Genesis, Rehovot, Israel), 0.125 μL (0.625 u) DreamTaq™

DNA polymerase (Fermentas, Vilnius, Lithuania), supplemented with its buffer (2.5 µL per reaction), dNTPs (2.5 mM each), and PCR-grade ddH$_2$O (Fisher Scientific, Wembley, Western Australia). The PCR amplification was performed in a Biometra Personal Cycler (Goettingen, Germany).

The PCR reaction program for ITS was as follows: 96° C. for 5 minutes, followed by 35 cycles of 96° C. for 45 seconds, 55° C. for 45 seconds, and 72° C. for 1 minute, followed by a 72° C. step for 5 minutes. The PCR reaction program for actin was similar to the PCR program of ITS, except that the denaturizing temperature was 95° C., the annealing temperature was 61° C., and the number of cycles was 40. The PCR products of ITS and actin (~500 bp and ~200 bp, respectively) were purified using the DNA Clean and Concentrator™ Kit (Zymo Research Corp., Irvine, CA, U.S.A), according to the manufacturer's instructions. Purified products were sent for direct PCR sequencing (Macrogen). The resultant sequences demonstrated that the tested fungus is a member of the genus *Daldinia*; both the ITS 5.8S rDNA region and the actin gene displayed 100% identity (99% coverage) to those of the *D. concentrica* published in the GenBank. A culture of the fungus was deposited on Jun. 23, 2008 under the Budapest Treaty in CBS culture collection in the protected cultures section under CBS123047 *Daldinia* sp. OBROB1A.

Example 3

This example demonstrates the identification of the volatile organic compounds using qualitative GC/MS analysis of *D. concentrica*.

*D. concentrica* was grown on PDB (5 mL) in sealed solid-phase microextraction (SPME) 20 mL vials. A Plug of growing mycelium was placed in each vial and incubated at 25° C. for at least three days. The volatiles were adsorbed for 30 minutes by automatic HS-SPME (headspace solid-phase microextraction) at 50° C. by 65 µm PDMS/DVB/CAR fiber (polydimethylsiloxane/divinylbenzene/carboxen) (Supelco Inc., Bellefonte, PA, USA). The fiber was inserted into the injection port of the GC-MS for 5 minutes (splitless) for desorption of the volatiles. GC-MS analysis was conducted according to the conditions described in Table 1.

TABLE 1

| | |
|---|---|
| Gas chromatograph | Agilent GC-MSD system (CA, USA) model 6890 or GCMS-TD model 7890 |
| Column | Rxi-5sil MS (Restek Bellefonte, PA, USA) |
| Injector temperature | 250° C. |
| Oven temperature | 50° C. (1 min), 5° C./min to 180° C., 25° C./min to 280° C. |
| Mass range | 41-350 |
| Gas | Constant pressure at 9.1 psi |
| Incubation - SPME | 15 min incubation at 40° C., 25 min extraction |
| Desorption time - SPME | 5 min splitless |
| EMV mode | Relative, 70 eV |
| MS Source, Quad auxiliary temperature | 230° C., 150° C., 280° C. |

The identification of the compounds was performed by comparing their relative retention indices and mass spectra with those of authentic standards or with those found in the literature and supplemented with Wiley8, Nist9, HC2205, and KI libraries.

Comparable analyses were conducted on SPME vials containing only PDB and these compounds were subtracted from the compounds obtained in *D. concentrica* containing vials. Final confirmatory identification of selected compounds was made by comparing the GC/MS data of authentic commercially available standards and published retention indices with the data from the fungal volatiles.

As shown in Table 2, below, 27 different compounds were identified that can be divided to several classes of chemicals substances: alcohols, dienes, ketones, aldehydes, and sesquiterpenes. Eight compounds: methyl-1,4-cyclohexadiene, phenyl ethyl alcohol, 3-methyl-1-butanol, (±)-2-methyl-1-butanol, 4-heptanone, 3-methoxy-2-naphthol, isoamyl acetate, and trans-2-octenal, suggested by the GC/MS analysis, were commercially available. It should be noted that although the fungus emitted 2-octenal of unknown stereochemistry, trans-2-octenal was actually tested because only the latter isomer was commercially available. The ability of these compounds to control the growth of *A. niger, B. cinerea, A. alternata*, and *P. digitatum*, was tested. It was found that only phenyl ethyl alcohol and 3-methoxy-2-naphthol failed to inhibit fungal growth. One compound, methyl-1,4-cyclohexadiene, exhibited poor growth inhibition of *A. niger* and *P. digitatum* (10.8% and 3.1%, respectively), and therefore was not further included in this study. Final identification of the five remaining chemical compounds: 3-methyl-1-butanol, (±)-2-methyl-1-butanol, 4-heptanone, isoamyl acetate, and trans-2-octenal, was done by comparison with authentic standards. The standards yielded identical retention times and mass spectra to the fungal products only to the first three chemical compounds, while the reminder two latter compounds have only been tentatively identified on the basis of databases comparisons. The abundances of the validated compounds were 5.9, 2.4, and 0.08 ppm for 3-methyl 1-butanol, (±)-2-methyl 1-butanol, and 4-heptanone, respectively. It is interesting to note that in contrast to *Muscodor albus*, another VOCs emitting endophytic fungi, the presence of the possibly carcinogenic naphthalene [23], was not identified among the *D. concentrica* VOCs

TABLE 2

| Retention time (min) | Suggested compound* | Molecular formula | Maine fragments (m/z) | Area (%) | MW |
|---|---|---|---|---|---|
| 2.2 | 3-methyl-1-butanol | C$_5$H$_{12}$O | 42, 55, 57, 70 | 1.0 | 88 |
| 2.25 | 2-methyl-1-butanol | C$_5$H$_{12}$O | 41, 56, 57, 70 | 1.1 | 88 |
| 2.7 | 1-methyl-1,3-cyclohexadiene | C$_7$H$_{10}$ | 77, 79, 91, 94 | 6.5 | 94 |
| 2.8 | 1-methyl-1,4-cyclohexadiene | C$_7$H$_{10}$ | 77, 79, 91, 94 | 3.9 | 94 |
| 4.1 | 4-heptanone | C$_7$H$_{14}$O | 43, 71, 114 | 0.2 | 114 |
| 4.3 | Isoamyl acetate | C$_7$H$_{14}$O$_2$ | | traces | 130 |

TABLE 2-continued

| Retention time (min) | Suggested compound* | Molecular formula | Maine fragments (m/z) | Area (%) | MW |
|---|---|---|---|---|---|
| 5.2 | 4-heptyn-2-ol | $C_7H_{12}O$ | 45, 53, 67, 68, 97, 112 | 4.2 | 112 |
| 5.5 | 2-octenal | $C_8H_{14}O$ | 42, 55, 57 84, 98, 126 | 33.3 | 126 |
| 6.3 | Octanal | $C_8H_{16}O$ | 69, 71, 72, 83, 84, 95, 110, 128 | 4.7 | 128 |
| 7.2 | 4,4-dimethyl-1,3-cyclopentanedione | $C_7H_{10}O_2$ | 41, 56, 126 | 4.0 | 126 |
| 7.7 | 2,2,5-trimethylcyclopentanone | $C_8H_{14}O$ | 41, 56, 126 | 16.5 | 126 |
| 10.5 | Phenyl ethyl alcohol | $C_8H_{10}O$ | 65, 91, 92, 122 | 1.9 | 122 |
| 18.2 | β-elemene | $C_{15}H_{24}$ | 41, 53, 55, 67, 68, 79, 81, 93, 107, 121, 133, 135, 147, 149, 161, 189, 204 | 0.06 | 204 |
| 18.4 | β-elemene | $C_{15}H_{24}$ | 41, 53, 55, 67, 68, 79, 81, 93, 107, 121, 133, 135, 147, 149, 161, 189, 204 | 1.0 | 204 |
| 19.4 | (+)-α-funebrene | $C_{15}H_{24}$ | — | traces | — |
| 19.6 | α-guaiene | $C_{15}H_{24}$ | 41, 53, 55, 67, 79, 81, 93, 105, 121, 133, 147, 161, 189, 204 | 0.1 | 204 |
| 19.9 | 2-(4-hydroxyphenyl)ethanol | $C_8H_{10}O_2$ | ? | 0.08 | 204 |
| 20.7 | Terpenes | $C_{10}H_{10}O_3$ | 108, 136, 137, 163, 178 | 9.0 | 178 |
| 21.0 | β-selinene | $C_{15}H_{24}$ | 41, 53, 55, 67, 79, 81, 91, 93, 107, 121, 133, 147, 161, 175, 189, 204 | 0.7 | 204 |
| 21.2 | α-selinene | $C_{15}H_{24}$ | 41, 53, 55, 67, 79, 81, 91, 93, 107, 121, 133, 147, 161, 175, 189, 204 | 0.2 | 204 |
| 21.4 | α-bulnesene | $C_{15}H_{24}$ | 41, 53, 55, 67, 79, 81, 91, 93, 107, 121, 133, 147, 161, 189, 204 | 0.7 | 204 |
| 21.6 | Germacrene A | $C_{15}H_{24}$ | — | traces | — |
| 21.8 | 7-epi-α-selinene | $C_{15}H_{24}$ | — | traces | — |
| 22.0 | Dauca-4(11),8-diene | $C_{15}H_{24}$ | — | traces | — |
| 22.9 | Veratryl acetone | $C_{11}H_{14}O_3$ | — | traces | — |
| 25.1 | 3-methoxy-2-naphthol | $C_{11}H_{10}O_2$ | 77, 131, 159, 174 | 1.6 | 174 |
| 25.2 | Pogostol | $C_{15}H_{26}O$ | 41, 53, 55, 71, 81, 93, 107, 121, 131, 147, 161, 189, 204 | 1.2 | 222 |

*Identification was carried out according to NIST Mass Spectral Library, ver. 2.0 d

Example 4

This example demonstrates the examination of the antimicrobial activity of D. concentrica and mixtures of same in vitro using the "Sandwich Method".

The "Sandwich Method" allows for no direct connection between D. concentrica and the test fungi. Thus, the effect of the former on the growth of the latter is only due to the volatiles produced by D. concentrica that spread freely across the plates.

A plug of PDA harboring the *D. concentrica* mycelia was added to 50 mm Petri dish containing 5 mL PDB and let to grow at 25° C. for three days for full inhibition of *Aspergillus niger* or for four days for full inhibition of *Alternaria alternata, Botrytis cinerea*, and *Penicillium digitatum*. Then, a plug of PDA harboring mycelia of the test fungus was added to another 50 mm Petri dish containing PDA, and the PDA Petri dish with the test fungus was put on top of the PDB containing Petri dish. Both Petri dishes were connected without their covers using parafilm and let to grow at 25° C. The effect of *D. concentrica* on the test fungi was examined after 2 days. The inhibitory effect of *D. concentrica* on various pathogenic fungi was examined similarly except that *D. concentrica* was grown for 6 days prior the addition of the test fungi and the inhibition was examined after 6 days of incubation. At the end of the assay, the viability of each test fungi was evaluated by transferring inoculum plugs to fresh PDA plates while observing the growth that developed within the next two days, as demonstrated in Table 3.

TABLE 3

| | Daldinia | | "Mixture 4"* | | "Mixture 21"* | |
|---|---|---|---|---|---|---|
| Pathogen | Growth inhibition | Viability | Growth inhibition | Viability | Growth inhibition | Viability |
| *Pythium ultimum* | 30.80 | + | 96.67 | – | 96.67 | – |
| *Pythium aphanidermatum* | 9.60 | + | 93.33 | – | 96.67 | – |
| *Alternaria alternata* pathotype tangelo | 100.0 | – | 100.0 | – | 100.0 | – |
| *Fusarium oxysporum* | 69.60 | + | 95.92 | + | 100.0 | – |
| *Fusarium euwallaceae* | 81.60 | + | 96.96 | + | 100.0 | – |
| *Fusarium mangiferae* | 100.0 | + | 100.0 | + | 100.0 | – |
| *Coniella* sp. | 100.0 | + | 100.0 | + | 100.0 | – |
| *Phoma tracheiphila* | 100.0 | – | 100.0 | – | 100.0 | – |
| *Colletotrichum* sp. | 100.0 | + | 100.0 | + | 100.0 | – |
| *Rhizoctonia solani* | 100.0 | – | 98.0 | + | 100.0 | – |
| *Alternaria alternata* | 100.0 | – | 100.0 | – | 100.0 | – |
| *Botrytis cinerea* | 100.0 | + | 100.0 | – | 100.0 | – |
| *Sclerotinia sclerotiorum* | 100.0 | – | 100.0 | – | 100.0 | – |
| *Penicillium digitatum* | 100.0 | – | 95.0 | + | 100.0 | – |
| *Lasiodiplodia theobromae* | 0.0 | + | 95.0 | + | 100.0 | – |
| *Neoscytalidium dimidiatum* | 100.0 | – | 94.0 | + | 100.0 | – |
| *Aspergillus niger* | 100.0 | – | 98.0 | + | 100.0 | – |

"Mixture 4" contains a bio-control agent comprising 3-methyl-1-butanol, (±)-2-methyl-1-butanol, 4-heptanone, and isoamyl acetate in a ratio of 1:1:2:1.
"Mixture 21" contains a bio-control agent comprising 4-heptanone and trans-2-octenal in a ratio of 1:1.

Example 5

This example demonstrates the examination of the bioactivity of *D. concentrica* under various temperatures.

The bioactivity of *D. concentrica* was examined under various temperatures in order to evaluate the ability of using the fungus in temperature controlled storage rooms. The lowest temperature that *D. concentrica* was able to grow and cause full inhibition of the test fungi *Alternaria alternata, Botrytis cinerea*, and *Penicillium digitatum* was 10° C.

Example 6

This example demonstrates the bioactivity of *D. concentrica* against *Aspergillus niger* (*A. niger*).

The bioactivity of *D. concentrica* was examined against *A. niger* in various volumes of sealed boxes. A 50 mm Petri dish containing 5 mL of PDB and a plug of PDA harboring *D. concentrica* mycelia was located in small (2.3 L), medium (7 L), and large (14 L) sealed boxes and let to grow without cover for three to five days at 25° C. Then, a plug of PDA harboring *A. niger* mycelia was transferred to a different 50 mm Petri dish containing PDA and the PDA Petri dish was quickly inserted into the sealed boxes containing *D. concentrica* and incubated for 7-10 days at 25° C. Similarly to the "Sandwich Method", also in this assay there is no direct connection between *D. concentrica* and the test fungus and only the VOCs of the former affect the growth of the latter.

*D. concentrica* fully inhibited the growth of *A. niger* under conditions of one (for small and medium boxes) or two (for the large boxes) 50 mm Petri plates containing *D. concentrica* grown for four days prior the addition of the test fungus.

Example 7

This example demonstrates the effect of the antimicrobial activity of the *D. concentrica* on food product spoilers.

The bioactivity of *D. concentrica* was examined against organic dried fruit inhabiting microorganisms. Appearance of pathogenic fungi on organic dried raisin and apricot was achieved by soaking the fruit in sterile double-distilled water for three hours followed by incubation at 25° C. for 6-9 days.

The results are presented in FIGS. 5A-C, wherein FIG. 5A represents dried fruit in the absence of *D. concentrica*; FIG. 5B represents dried fruit in the presence of one 50 mm Petri plate containing *D. concentrica* grown on PDB; and FIG. 5C represents dried fruit in the presence of two 50 mm Petri plates containing *D. concentrica* grown on PDB.

The appearance of pathogenic fungi such as *Rhizopus* sp., *Penicillium* sp., and *Aspergillus* sp. on those fruits is demonstrated by FIGS. 5A-C. Exposure of the swelled fruit to a 4 days old *D. concentrica* culture grown in one as demonstrated by FIG. 5B or two as demonstrated by FIG. 5C 50 mm Petri plate containing 5 mL PDB abolished the appearance of all pathogenic fungi. The bioassay was performed in a sealed 1 L box preventing direct contact between *D. concentrica* and the examined fruit.

The bioactivity of *D. concentrica* was further examined against the growth of *Penicillium digitatum* (hereinafter *P. digitatum*) on tomato paste. A commercial tomato paste was inoculated with *P. digitatum* mycelium at 4-6 spots and incubated at 25° C.

The results are presented in FIGS. 6A-C wherein FIG. 6A represents inoculated tomato paste in the absence of *D. concentrica*; FIG. 6B represents inoculated tomato paste in the presence of one 50 mm Petri plate containing *D. concentrica* grown on PDB; and FIG. 6C represents inoculated tomato paste in the presence of two 50 mm Petri plates containing *D. concentrica* grown on PDB.

After three days *P. digitatum* mycelium covered the surface of the tomato paste as demonstrated by FIG. 6A. However, in the presence of 4 days old *D. concentrica* culture grown in one as demonstrated by FIG. 6B or two as demonstrated by FIG. 6C 50 mm Petri plate containing 5 mL PDB, no mycelium of the pathogenic fungi was observed.

The bioactivity of *D. concentrica* was further examined against the growth of *A. niger* on peanuts. The peanuts were placed in 50 mm Petri plate containing 5 mL water and inoculated with drops (10 µL; 3 drops per each peanut) of conidial suspension ($10^6$ conidia/mL) and incubated at 25° C.

The results are presented in FIGS. 7A-C wherein FIG. 7A represents inoculated peanut in the absence of *D. concentrica*; FIG. 7B represents inoculated peanuts in the presence of one 50 mm Petri plate containing *D. concentrica* grown on PDB; FIG. 7C represents inoculated peanuts in the presence of two 50 mm Petri plates containing *D. concentrica* grown on PDB.

After 10 days all the peanuts were germinated and covered with *A. niger* as demonstrated by FIG. 7A. The presence of 5 days old *D. concentrica* culture grown in one as demonstrated by FIG. 7B or two as demonstrated by FIG. 7C 50 mm Petri plate containing 5 mL PDB, prevented *A. niger* growth on the peanuts, however, *D. concentrica* did not affect peanut germination.

The bioactivity of *D. concentrica* was further examined against the growth of *P. digitatum* on oranges. The oranges were inoculated with *P. digitatum* in sealed 2 L boxes without *D. concentrica* or in the presence of 4 days old *D. concentrica* culture grown in 25° C.

Referring to FIGS. 8A-D wherein FIG. 8A represents inoculated oranges in the absence of *D. concentrica*; FIG. 8B represents inoculated oranges in the presence of one 50 mm Petri plate containing *D. concentrica* grown on PDB; FIG. 8C represents inoculated oranges in the presence of two 50 mm Petri plates containing *D. concentrica* grown on PDB; FIG. 8D represents inoculated oranges in the presence of three 50 mm Petri plates containing *D. concentrica* grown on PDB.

The inoculation was performed by deposition of 10 µL drops of spore suspension ($10^4$ spores/mL) on pre-injured peel and incubation at 25° C. for 17 days. As shown in FIGS. 8A-D, only the presence of three Petri plates of *D. concentrica* abolished *P. digitatum* growth whereas the presence of one or two Petri plates of the fungi resulted in reduction of the symptoms relative to the control.

Example 8

This example demonstrates the effect of the antimicrobial activity of *D. concentrica* on plant pathogenic nematodes.

The bioactivity of *D. concentrica* was examined against J2 larvae of the plant pathogenic nematode *Meloidogyne javanica*. *D. concentrica* was grown in one, two, or three 50 mm Petri plate containing 5 mL PDB at 25° C. for 5 days. Then, in a 1 L sealed box, 300 *M. javanica* J2 larvae were introduced to the fungus VOCs and incubated in the dark at 25° C. After two days, the larvae were transferred to 20 µm filter and incubated for 3 hours at 25° C. in the dark. This filtration differentiates between live and dead larvae—only live larvae would actively pass the filter whereas dead larvae would be stuck on the filter. In the end of the incubation only the live larvae were counted. As shown in FIG. 9, *D. concentrica* significantly reduced the number of viable *M. javanica* J2 larvae, and this effect was achieved already in the presence of one Petri dish culture of *D. concentrica*.

Example 9

This example demonstrates the effect of the antimicrobial activity of mixtures of the emitted VOCs against agricultural pathogens and pests such as fungi and nematodes.

The antimicrobial activity of "Mixture 4" was tested against plant pathogenic fungi as described in Table 3. The antimicrobial activity of "Mixture 4" was examined also in various temperatures against four plant pathogenic fungi: *A. niger, Botrytis cinerea, Alternaria alternata* and *Penicillium digitatum*. Fungal growth was monitored for 14 days. This bioassay was performed in sealed 1 L box that contained four 50 mm Petri plates each containing PDA and a plug of the test fungi and on the opposite side one small vial (10 mm width×35 mm height) containing 1 mL of "Mixture 4". As shown in FIG. 10, "Mixture 4" inhibited or abolished the growth of the test fungi at all temperatures tested.

The antimicrobial activity of "Mixture 21" was tested against plant pathogenic fungi as described in Table 3. Similarly to "Mixture 4", the antimicrobial activity of "Mixture 21" was examined in various temperatures against the same four plant pathogenic fungi. The bioassay was conducted as for "Mixture 4" with one exception: instead of using vials to contain the mixture, 50 µL of "Mixture 21" was loaded on blotting paper and put inside the sealed box. As shown in FIG. 11, after 14 days none of the test fungi grew in the presence of "Mixture 21" at all temperatures tested.

The bioactivity of "Mixture 4" was further examined against J2 larvae of the plant pathogenic nematode *Meloidogyne javanica*. The bioassay was performed in 1 L sealed box. Each box contained 5 vials (10 mm width×35 mm height) each containing 300 J2 larvae in 0.01 M MES (2-(N-morpholino)ethanesulfonic acid), one identical vial containing 1 mL of "Mixture 4", and one 50 mm Petri plate containing 5 mL of double distilled sterile $H_2O$ for moisture supply. The nematodes were incubated with or without "Mixture 4" for 2 days in the dark at 25° C. and then transferred to a 20 µm filter and incubated for 3 hours at 25° C. in the dark for the separation between live and dead nematodes. Only the live larvae were counted at the end of the incubation time. "Mixture 4" caused a dramatic decrease in the number of live larvae: J2s viability (11.4+4.0%). This result suggests that the effect of the synthetic mixture on larvae viability is more potent than the effect resulted by the fungal culture plate (FIG. 12).

The bioactivity of "Mixture 4" was further examined against the growth of *A. niger* and *P. digitatum* on peanuts. The peanuts were placed in 50 mm Petri plate containing 5 mL of water and inoculated with drops (10 μL; 3 drops per each peanut) of conidial suspension ($10^6$ conidia/mL) of each fungus and incubated at 25° C. in sealed 1 L boxes.

The results are presented in FIGS. 13A-F wherein FIG. 13A represents peanuts inoculated with *A. niger* in the presence of 1 mL/L "Mixture 4". FIG. 13B represents peanuts inoculated with *A. niger* without "Mixture 4". FIG. 13C represents peanuts inoculated with *P. digitatum* in the presence of 1 mL/L "Mixture 4". FIG. 13D represents peanuts inoculated with *P. digitatum* without mixture. FIG. 13E represents non-inoculated peanuts in the presence of 1 mL/L "Mixture 4". FIG. 13F represents non-inoculated peanut without "Mixture 4".

After 10 days, all the peanuts exposed to "Mixture 4" were free of any infection symptoms, i.e., no fungus was observed as demonstrated by FIGS. 13 A, C, E, whereas *A. niger* growth was clearly observed in both control and pre-inoculated peanuts in the absence of "Mixture 4" as demonstrated by FIG. 13 B, D, F.

The bioactivity of "Mixture 4" was further examined against the prevention of disease symptoms in grapes inoculated or non-inoculated with the pathogenic fungus *Botrytis cinerea*. Grapes were stored in sealed 2 L boxes in the presence of two concentrations of "Mixture 4" (1 or 2 mL/L) or in absence of "Mixture 4" as a control. In addition, half of the grapes were pre-inoculated with conidial suspension of *B. cinerea* ($4.5 \times 10^5$ conidia/mL) whereas the other half was not treated in order to examine the effect of "Mixture 4" on natural inoculation. The grapes were exposed to "Mixture 4" for either 4 or 12 days at 0° C. Then, the vials containing "Mixture 4" were removed and the boxes were opened for 10 minutes at room temperature, enabling VOCs to evaporate before returning them to 0° C. for further incubation. After 1 month, all boxes were opened and transferred to 20° C. for two days and then the number of *B. cinerea* infected grapes was counted.

The results are presented in FIGS. 14A-B, wherein FIG. 14A demonstrates the effect of "Mixture 4" on disease symptoms of pre-inoculated grapes. FIG. 14B demonstrates the effect of "Mixture 4" on disease symptoms of non-treated grapes. FIG. 14A demonstrates that high concentration of "Mixture 4" prevented *B. cinerea* infection already after 4 days of exposure, whereas natural infection of the grapes by *B. cinerea* was significantly reduced in the presence of both low and high concentrations of the mixture in both 4 and 12 days of exposure, as demonstrated by FIG. 14B.

Example 10

This example demonstrates the bioactivity of "Mixture 4" as a fumigant in storage of wheat.

Commercial wheat grains were incubated in sealed 1 L boxes with or without moisture in the presence of increasing concentrations (0, 0.75, 1, and 1.25 μL/mL) of "Mixture 4" at 25° C. for 6 days and then 5 wheat grains were randomly collected from the boxes and transferred to PDA Petri plates and further incubated at 25° C. for 5 days in order to isolate fungi colonizing the wheat grains.

Figures 15A, 15B, 15C, 15D, 15E:
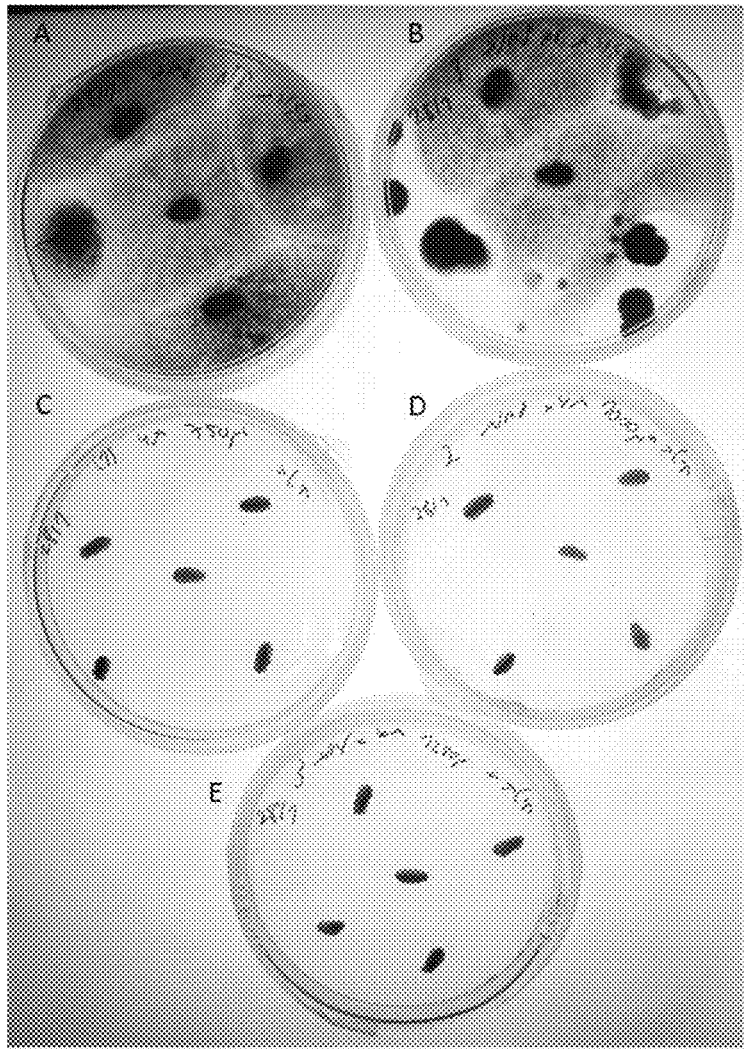

The results are presented in FIGS. 15A-E, wherein FIG. 15A demonstrates fungal isolation from non-treated wheat grains. FIG. 15B demonstrates fungal isolation from non-treated wheat grains that were incubated in the presence of moisture. FIG. 15C demonstrates fungal isolation from wheat grains incubated in the presence of moisture and exposed to 0.75 μL/mL of "Mixture 4". FIG. 15D demonstrates fungal isolation from wheat grains incubated in the presence of moisture and exposed to 1 μL/mL of "Mixture 4". FIG. 15E demonstrates fungal isolation from wheat grains incubated in the presence of moisture and exposed to 1.25 μL/mL of "Mixture 4". As shown in FIGS. 15A-E, fungal isolation occurred only in the absence of "Mixture 4", suggesting that this mixture is a powerful fumigant.

Example 11

This example demonstrates the bioactivity of "Mixture 4" against the growth of *P. digitatum* on oranges.

The oranges were inoculated with the pathogenic fungus in sealed 2 L boxes in the presence of increasing concentrations (0, 0.125, 0.25, and 0.375 μL/mL) of "Mixture 4" at 25° C. for 7 days.

The results are presented in FIGS. 16A-E, wherein FIG. 16A represents non-treated oranges. FIG. 16B represents oranges inoculated with *P. digitatum* in the absence of "Mixture 4". FIG. 16C represents oranges inoculated with *P. digitatum* in the presence of 0.125 μL/mL of "Mixture 4". FIG. 16D represents oranges inoculated with *P. digitatum* in the presence of 0.25 μL/mL of "Mixture 4". FIG. 16E represents oranges inoculated with *P. digitatum* in the presence of 0.375 μL/mL of "Mixture 4". As demonstrated in FIGS. 16A-E, at the lowest concentration, "Mixture 4" reduced symptom severity whereas in higher concentrations the presence of "Mixture 4" prevented symptoms appearance.

Example 12

This example demonstrates the bioactivity of "Mixture 21" against plant aphids in vitro and in planta.

The examined aphids were: green peach aphid *Myzus persicae, Aphis gossypii* from Cucurbitaceae, the cabbage aphid *Brevicoryne brassicae*, the oleander aphid, *Aphis nerii*, the silverleaf whitefly *Bemisia tabaci*, and the corn leaf aphid, *Rhopalosiphum maidis*. Each aphid was transferred to 90 mm Petri plates and exposed to variable concentrations of "Mixture 21" (0, 0.125, 0.25, and 0.5 μL/mL) for 15 minutes at room temperature. Then, the viability of the aphids was examined under binocular and compared to non-exposed aphids.

As shown in FIG. 17, the death of the aphids was observed already in the lowest concentration of "Mixture 21". All the aphids that were not exposed to "Mixture 21" were alive.

FIG. 18 demonstrates the effect of "Mixture 21" on cucumber plants (*Cucumis sativus*) infested by *Bemisia tabaci* aphid. The plants were exposed to "Mixture 21" for 15 minutes before evaporation of VOCs.

Cucumber plants were inoculated with silverleaf whitefly *Bemisia tabaci* and then each plant was sealed in a plastic bag in the presence of increasing concentrations of "Mixture 21" (0, 0.041, 0.083, and 0.125 μL/mL) at room temperature. After 15 minutes of exposure to "Mixture 21", all aphids were dead, and the plants were removed from the sealed bags for VOCs evaporation. Next, the plants were left to grow at room temperature and symptoms of phytotoxicity were monitored. As shown in FIG. 18, there was no visible difference between plants that were exposed to "Mixture 21"

and control plants, suggesting low phytotoxicity of "Mixture 21" under the tested conditioned.

Example 13

This example demonstrates the bioactivity of "Mixture 21" against sprouting of potatoes during storage.

The potatoes were incubated in sealed 2 L boxes in the presence of increasing concentrations (0, 0.005, 0.0125, 0.025, and 0.05 μL/mL) of "Mixture 21" at 20° C. for 10 days in the dark.

The results are presented in FIGS. 19A-E, wherein FIG. 19A represents non-treated potatoes. FIG. 19B represents potatoes in the presence of 0.005 μL/mL of "Mixture 21". FIG. 19C represents potatoes in the presence of 0.0125 μL/mL of "Mixture 21". FIG. 19D represents potatoes in the presence of 0.025 μL/mL of "Mixture 21". FIG. 19E represents potatoes in the presence of 0.05 μL/mL of "Mixture 21". As demonstrated in FIG. 19, at the two lowest concentrations, "Mixture 21" reduced potatoes' sprouting relative to the control whereas in the higher concentrations, the presence of "Mixture 21" prevented the sprouting.

Example 14

This example demonstrates that 4-heptanone possesses nematicidal activity toward *M. javanica* J2 larvae.

The effects of *D. concentrica*, synthetic mixture and the pure compound 4-heptanone were also examined visually under a stereomicroscope. The results are presented in FIGS. 20A-D wherein FIG. 20A represents non-treated nematodes; FIG. 20B represents nematodes exposed to three *D. concentrica* culture plates (50 mm in diameter with 5 mL growth medium) pre-grown for 4 days; FIG. 20C represents nematodes exposed to 0.25 mL/L of synthetic mixture preloaded to 125 mg of perlite particles; FIG. 20D represents nematodes exposed to 0.05 mL/L of the compound 4-heptanone preloaded to 25 mg of perlite particles. Most of the control nematodes remained mobile possessing the characteristic sinusoidal or curve like shape of viable nematodes. In contrast, after exposure to *D. concentrica* culture plates, a clear reduction in the number of viable nematodes was observed as shown by relatively higher distribution of nematodes with straight shapes body Moreover, after exposure to either the mixture or to 4-heptanone, most of the nematodes demonstrated the typical straight body shape with nearly no curved appearance, implying on their mortality (FIG. 20B-D).

Example 15

This example demonstrates that *M. javanica* eggs are affected by the synthetic mixture.

Since both the fungus and the synthetic mixture affected the viability of J2 larvae (FIG. 12), the susceptibility of *M. javanica* eggs was examined. As shown in FIG. 21, the number of viable J2s larvae that hatched from *M. javanica* eggs exposed to *D. concentrica* was similar to the number obtained under control, non-exposed conditions. However, the synthetic mixture led to significant reduction in the viability of the larvae, suggesting a strong nematicidal activity of the synthetic mixture compared with *D. concentrica* culture.

Example 16

This example demonstrates that application of the synthetic mixture into nematode infested soil reduces disease occurrence.

In order to examine the ability of the synthetic mixture to prevent disease development, the synthetic mixture was tested for use in reducing J2 larvae viability in soil. To this end, the soil was mixed with perlite particle pre-loaded with increasing volumes of the mixture, and then *M. javanica* J2 larvae were added to the treated soil. As shown in FIG. 22, the mixture significantly reduced larvae viability at concentration as low as 0.083 μL/g soil. This result suggests that the mixture is efficient against the nematodes in soil. Next, susceptible tomato seedlings were inoculated with the nematodes in the presence or absence of the synthetic mixture, and after 7-8 weeks disease occurrence was evaluated by galling index, root weight, and the number of *M. javanica* eggs per gram root. The results are presented in FIGS. 23A-C wherein FIG. 23A represents galling index; FIG. 23B represents number of *M. javanica* eggs per gram of root; FIG. 23C represents root weight. Inoculated tomato plants grown in treated soil that was exposed to the synthetic mixture presented significantly lower galling index and number of nematode eggs per gram root, while there was no significant difference in the root weight between exposed and non-exposed plants. Taking together, the present results suggest that the synthetic mixture, based on four of *D. concentrica* volatiles, might provide a new strategy to combat RKN disease.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition comprising: (a) synthetic trans-2-octenal, (b) non-ionic or anionic surfactant, and (c) soil.

2. The composition of claim 1, further comprising 3-methyl-1-butanol, (±)-2-methyl-1-butanol, 4-heptanone, and isoamyl acetate.

3. The composition of claim 2, wherein said 3-methyl-1-butanol, (±)-2-methyl-1-butanol, 4-heptanone, and isoamyl acetate are in a ratio of 1:1:2:1.

4. A method of killing a phytopathogenic fungus, reducing growth of said phytopathogenic fungus, or reducing overall damage to a plant or a plant part caused by said phytopathogenic fungus, comprising exposing said phytopathogenic fungus to a composition comprising a non-ionic or anionic surfactant and an antifungally effective amount of synthetic trans-2-octenal, thereby killing said phytopathogenic fungus, reducing growth of said phytopathogenic fungus, or reducing overall damage to a plant or a plant part caused by said phytopathogenic fungus.

5. The method of claim 4, wherein said plant or said plant part is pre-harvested.

6. A method for soil planting a plant or seed in soil that may be contaminated by a phytopathogenic fungus, comprising the consecutive steps of: (a) inoculating said soil, comprising contacting said soil with an antifungally effective amount of trans-2-octenal, and (b) planting a plant or a seed thereby soil planting.

7. The method of claim 4, wherein said exposing comprises: immersing, coating, dipping, spraying, evaporating, fogging, scattering, painting on and/or injecting.

8. A composition according to claim 1, wherein said trans-2-octenal is present in said soil in an antifungally effective amount.

9. A method for protecting a plant or a seed from damage by a phytopathogenic fungus, comprising inoculating soil with an antifungally effective amount of trans-2-octenal, and planting a plant or a seed in said soil either prior to or subsequent to said inoculating step, such that said plant or seed grows in said inoculated soil.

10. The method of claim 4, wherein said phytopathogenic fungus is of the species *S. rolfsii*.

11. The method of claim 5, wherein said phytopathogenic fungus is of the species *S. rolfsii*.

12. The composition of claim 8, wherein said trans-2-octenal is present in said soil in an amount that is antifungally effective against fungus of the species *S. rolfsii*.

13. The method of claim 9, wherein said phytopathogenic fungus is of the species *S. rolfsii*.

* * * * *

SEQUENCE LISTING

```
<160> NUMBER OF SEQ ID NOS: 6

<210> SEQ ID NO 1
<211> LENGTH: 562
<212> TYPE: DNA
<213> ORGANISM: Daldinia sp.

<400> SEQUENCE: 1
```

```
ctgcggaggg atcattaccg agttatctaa actccaaccc tttgtgaacc ttaccgtcgt      60
tgcctcggcg ggctgcgctt accctgtagc taccctgtag ctaccggta  ggcgcgctcc     120 aagcccgccg gtggaccact aaactctgtt ttaataccga atctctgaat gcttcaactt     180
aataagttaa aactttcaac aacggatctc ttggttctgg catcgatgaa gaacgcagcg     240
aaatgcgata agtaatgtga attgcagaat tcagtgaatc atcgaatctt gaacgcaca     300 ttgcgcccat tagtattcta gtgggcatgc ctattcgagc gtcatttcaa cccttaagcc     360
ttagttgctt agcgttggga gtctgcgctg tacttgttac ggcgcagttc ctcaaagtga     420
ttggcggagt tagggcatac tctaagcgta gtaatatttc ttctcgcttc tgtagttgtc     480
ctggcggctt gccgttaaac ccctatattt tctagtggtt gacctcggat taggtaggaa     540
tacccgctga acttaagcat at                                              562

<210> SEQ ID NO 2
<211> LENGTH: 211
<212> TYPE: DNA
<213> ORGANISM: Daldinia sp.

<400> SEQUENCE: 2
tggcccatac caatcatgat actagcatat tgttagatat cgtcgtgcgc ggctatatat      60
gtatatcgga tcaactactt acccatggtg gcggggacga ccaacgatgg acgctgtatt     120
aatatgttag aaaagaatac aaacttgggc ccgttctgat gaggccgaag cggggcgat     180 ggttgggcga ggatggaact tacggaaaac a                                    211

<210> SEQ ID NO 3
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 3
tccgtaggtg aacctgcggg                                                  20

<210> SEQ ID NO 4
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 4
tcctccgctt attgatatgc                                                  20

<210> SEQ ID NO 5
<211> LENGTH: 20
<212> TYPE: DNA
<213> ORGANISM: Artificial Sequence
<220> FEATURE:
<223> OTHER INFORMATION: Single strand DNA oligonucleotide

<400> SEQUENCE: 5
tcctccgctt attgatatgc                                                  20

<210> SEQ ID NO 6
<211> LENGTH: 20
<212> TYPE: DNA
<213> ORGANISM: Artificial Sequence
<220> FEATURE:
```

```
<223> OTHER INFORMATION: Single strand DNA oligonucleotide

<400> SEQUENCE: 6
tacgagtcct tctggcccat                                              20
```